(12) United States Patent
Szeto

(10) Patent No.: US 7,550,439 B2
(45) Date of Patent: *Jun. 23, 2009

(54) METHODS FOR REDUCING OXIDATIVE DAMAGE

(75) Inventor: Hazel H. Szeto, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 199 days.

This patent is subject to a terminal disclaimer.

(21) Appl. No.: 11/040,242

(22) Filed: Jan. 21, 2005

(65) Prior Publication Data

US 2006/0084606 A1    Apr. 20, 2006

Related U.S. Application Data

(60) Provisional application No. 60/538,841, filed on Jan. 23, 2004.

(51) Int. Cl.
*A61K 38/07* (2006.01)
(52) U.S. Cl. .......................................... 514/18; 530/330
(58) Field of Classification Search ........................ None
See application file for complete search history.

(56) References Cited

U.S. PATENT DOCUMENTS

| | | | |
|---|---|---|---|
| 5,312,899 | A | 5/1994 | Schiller |
| 5,602,100 | A | 2/1997 | Brown et al. |
| 5,652,122 | A | 7/1997 | Frankel et al. |
| 5,885,958 | A | 3/1999 | Zadina |
| 5,993,848 | A * | 11/1999 | Suzuki et al. ............... 424/449 |
| 5,994,372 | A | 11/1999 | Yaksh |
| 6,221,355 | B1 | 4/2001 | Dowdy |
| 6,268,398 | B1 | 7/2001 | Ghosh et al. |
| 6,503,713 | B1 | 1/2003 | Rana |
| 6,703,483 | B1 | 3/2004 | Schiller |
| 6,759,520 | B1 * | 7/2004 | Carr et al. ................... 530/402 |
| 6,900,178 | B2 | 5/2005 | Oeltgen et al. |
| 2004/0248808 | A1 | 12/2004 | Szeto et al. |
| 2005/0096333 | A1 | 5/2005 | Dugar et al. |
| 2005/0192215 | A1 | 9/2005 | Ghosh et al. |
| 2007/0129306 | A1 | 6/2007 | Szeto et al. |

FOREIGN PATENT DOCUMENTS

| | | |
|---|---|---|
| CA | 2361364 | 9/2000 |
| WO | WO 9522557 | 8/1995 |
| WO | WO 00/55189 | 9/2000 |
| WO | WO 02/05748 | 1/2002 |

OTHER PUBLICATIONS

Rudinger, J (1976). Peptide Hormones (Ed. J.A. Parson). University Park Press. baltomre pp. 1-7.*
Bradley et al. 'Limits of Cooperativeity in a Structurally Modula Protein: Response of the Notch Ankyrin Domain to Analogous Alanine Substitution in Each Repeat.' J. Mol. Biol. vol. 324, pp. 373-386. 2002.*
Ngo et al. "Computational Complexity, Protein Structure Prediction, and the Levinthal Paradox." TheProtein Folding Problem and Tertiary structure Prediction. Ed. K. Merz and L. Le Grand. Birkhauser, Boston, Ma. 491-495.*
Berendsen, Herman. "A Glimpse of the Holy Grail?" Science, vol. 282, pp. 642-643. Oct. 23, 1998.*
File Medline on STN An No. 2005478947. Simmons, Zachary. "Management Strageies for Patients with Amyotrphoic Lateral Sclerosis from diagnosis Through Death." The Neurologist (Sep. 2005), vol. 11, No. 5, pp. 257-270. Abstract only.*
Azzouz, Mimoun "Gene Therapy for ALS: Progress and Prospects" Biochemical et Biophysica Acta (2006), vol. 1762 pp. 1112-1127.*
Pages et al. 'Cystamine and Cysteamine Increase Brain Levels of BDNF in Huntington Disease VIA HSJ1b and Transglutaminase' J. of Clin. Invest. vol. 116 No. 5, pp. 1410-1424. May 2006.*
Margolis et al. 'Diagonsis of Huntington Disease' Clinical Chemistry, vol. 49, No. 10 pp. 1726-1732 (2003).*
Korczyn et al. 'Emerging Therapies in the Pharmacological Treatment of Parkinson's Disease' Drugs vol. 62, No. 5 pp. 775-786. 2002.*
Sriram et al. 'Experimental Allergic Encephalomyetlitis: A Misleading Model of Multiple Sclerosis' Ann. Neurol. vol. 58, pp. 939-945. 2005.*
Steinman et al. 'How to Successfully Apply Animal Studies in Experimental Allergic Encephalomyelitis to Research on Multple Sclerosis' Ann Neurol. vol. 60, pp. 12-21. 2006.*
Citron, Martin. 'Alzheimer's Disease: Treatment in Discovery and Development' Nature Nuerosicence Supplment. vol. 5. pp. 1055-1057. Nov. 2002.*
Patel et al. 'Pharmacotherapy of Cognitive Impariment in Alzheimer's Disease: A Review' J. Geriatr. Psychiatry Neruol. vol. 8 pp. 81-95. 1995.*
Clapp III, et al. "Cardiovascular and Metabolic Responses to Two Receptor-Selective Opioid Agonists in Pregnant Sheep", Am. J. Obstet. Gynecol., vol. 178, No. 2 (Feb. 1998) pp. 397-401.
Holsey, et al. "Cardiovascular Effects of a μ-Selective Opioid Agonist (Tyrosine-D-Arginine-Phenylalanine-Lysine-$NH_2$) in Fetal Sheep: Sites and Mechanisms of Action", Am. J. Obstet. Gynecol., vol. 180, No. 5 (May 1999) pp. 1127-1130.

(Continued)

*Primary Examiner*—Anish Gupta
(74) *Attorney, Agent, or Firm*—Foley & Lardner LLP

(57) ABSTRACT

The invention provides a method for reducing oxidative damage in a mammal, a removed organ, or a cell in need thereof. The method comprises administering an effective amount of an aromatic cationic peptide. The aromatic cationic peptide has (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a or 2a is the largest number that is less than or equal to $p_t+1$, except that when a is 1, $p_t$ may also be 1; and (f) at least one tyrosine or tryptophan amino acid.

24 Claims, 24 Drawing Sheets

OTHER PUBLICATIONS

Kett, et al. "Baroreflex-Mediated Bradycardia but Not Tachycardia is Blunted Peripherally by Intravenous μ-opioid Agonists", Am. J. Obstet. Gynecol., vol. 178, No. 5 (May 1998) pp. 950-955.

Neilan, et al. "Pharmacological Characterization of the Dermorphin Analog [Dmt[1]]DALDA, a Highly Potent and Selective μ-Opioid Peptide", European Journal of Pharmacology, vol. 419, Issue 1 (2001) 15-23.

Omoniyi, et al. "A Peripheral Site of Action for the Attenuation of Baroreflex-Mediated Bradycardia by Intravenous μ-Opioid Agonists", Journal of Cardiovascular Pharmacology™, vol. 35, No. 2 (2000) pp. 269-274.

Schiller, et al. "Dermorphin Analogues Carrying an Increased Positive Net Charge in Their "Message" Domain Display Extremely High μ Opioid Receptor Selectivity", Journal of Medicinal Chemistry, vol. 32, No. 3 (1989) pp. 698-703.

Schiller, et al. "Synthesis and In Vitro Opioid Activity Profiles of DALDA Analogues", European Journal of Medicinal Chemistry, vol. 35, Issue 10 (Oct. 2000) pp. 895-901.

Shimoyama, et al. "Antinociceptive and Respiratory Effects of Intrathecal H-Tyr-D-Arg-Phe-Lys-$NH_2$ (DALDA) and [Dmt[1]] DALDA", The Journal of Pharmacology and Experimental Therapeutics, vol. 297, No. 1 (Apr. 2001) pp. 364-371.

Szeto, et al. "In Vivo Disposition of Dermorphin Analog (DALDA) in Nonpregnant and Pregnant Sheep", The Journal of Pharmacology and Experimental Therapeutics, vol. 284, No. 1 (1998) pp. 61-65.

Szeto et al. "Respiratory Depression After Intravenous Administration of δ-Selective Opioid Peptide Analogs", Peptides, vol. 20 (1999) pp. 101-105.

Szeto, et al. "Mu-Opioid Receptor Densensitization and Resensitization In Vivo", International Narcotics Research Conference, Poster Abstracts, Monday (1999) Mon19, p. 5.

Szeto, et al. "In Vivo Pharmacokinetics of Selective μ-Opioid Peptide Agonists", The Journal of Pharmacology and Experimental Therapeutics, vol. 298, No. 1 (Jul. 2001) pp. 57-61.

Wu, et al. "Myocardial Protective Effect of Mu Opioid Agonists", International Narcotics Research Conference, Poster Abstracts, Sunday (1999) Sun59, p. 15.

Zhao, et al. "Transcellular Transport of a Highly Polar 3+ Net Charge Opioid Tetrapeptide", The Journal of Pharmacology and Experimental Therapeutics, vol. 304, (2003) pp. 425-432.

Zhao, et al. "Translocation of a 3+ Net Charge Tetrapeptide Across Plasma Membrane of Mammalian Cells", World Congress of Pharmacology, Abstract, Published May 1, 2002.

Zhao, et al., "Profound Spinal Tolerance After Repeated Exposure to a Highly Selective μ-Opioid Peptide Agonist: Role of σ-Opioid Receptors", vol. 302, (2002) pp. 188-196.

Wu, et al. "A highly potent peptide analgesic that protects against ischemia-reperfusion-induced myocardial stunning", Am. J. Physiol. Heart Circ. Physiol, 283: H-783-H791 (2002).

Broekemeier, et al., "Inhibition of the Mitochondrial Permeability Transition by Cyclosporin A during Long Time Frame Experiments: Relationship between Pore Opening and the Activity of Mitochondrial Phospholipases", Biochemistry 1995, 34:16440-16449.

Zadina J. et al., "A Potent and Selective Endogeneous Agonist for the Mu-Opiate Receptor", Nature, Nature Publishing Group, London, GB, vol. 386, Apr. 3, 1997, pp. 499-502, XP002072008.

Spetea, Mariana et al., "Interaction of agonist peptide (3H) Tyr-D-Ala-Phe-Phe-NH2 with mu-opioid receptor in rat brain and CHO-mu/1 cell line", Peptides (New York), vol. 19, No. 6, 1998, pp. 1091-1098, XP002410285.

Dooley, C T et al., "Selective ligands for the mu, delta and kappa opioid receptors identified from a single mixture based tetrapeptide positional scanning combinatorial library", Journal of Biological Chemistry, American Society of Biochemistry and Molecular Biology, Birmingham, US, vol. 273, No. 30, Jul. 24, 1998, pp. 18848-18856 XP002100725.

Schiller, P.W. et al., "Opioid peptide analogs with novel activity profiles as potential therapeutic agents for use in analgesia", STN CAPLUS, No. 132:102403, 1997, XP002933635.

Bork, "Powers and Pitfalls in Sequence Analysis: The 70% Hurdle", 2000, Genome Research 10:398-400.

Skolnick et al., "From genes to protein structure and function: novel applications of computational approaches in the genomic era", 2000, Trends in Biotech. 18(1):34-39.

Doerks et al., "Protein annotation: detective work for function prediction", 1998, Trends in Genetics 14:248-250.

Smith et al., "The challenges of genome sequence annotation or 'The devil is in the details'", 1997, Nature Biotechnology 15: 1222-1223.

Brenner, "Errors in genome annotation", 1999, Trends in Genetics 15:132-133.

Bork et al., "Go hunting in sequence databases but watch out for the traps", 1996, Trends in Genetics 12:425-427.

Lishmanov et al., "Ligands for Opioid and δ-Receptors Improve Cardiac Electrical Stability in Rat Models of Post-Infarction Cardiosclerosis and Stress", Life Sciences. 1999; 65: PL 13-17.

Demas et al., "Anaesthesia for Heart Transplantation", Br J Anaesth. 1986; 58: 1357-1564.

Shroff et al., "Effects of Intrathecal Opioid on Extubation Time, Analgesia, and Intensive Care Unit Stay Following Coronary Artery Bypass Grafting", Journal of Clinical Anesthesia. 1997;9: 415-419.

Lasukova et al., "Activation of mu-opioid receptors and cardiomyocyte resistance to free radical damage", Patol Fiziol Eksp Ter. 2001 2: Abstract Only; article in Russian.

Song et al., "A potent opiate agonist protects against myocardial stunning during myocardial ischemia and reperfusion in rats", Coronary Artery Disease, 2005; 16: 407-410.

Drin et al., "Studies on the Internalization Mechanism of Cationic Cell-penetrating Peptides", Journal of Biological Chemistry, 2003, 278:33, 31192-31201.

Richard et al., "Cell-penetrating Peptides", Journal of Biological Chemistry, 2003: 278:1, 585-590.

Schwarze, Steven R., et al., "In vivo Protein Transduction: Intracellular Delivery of Biologically Active Proteins, Compounds and DNA", Trends In Pharmacological Sciences, 2000, 21:45-48.

Dimaio, et al., "Synthesis and Pharmacological Characterization in Vitro of Cyclic Enkephalin Analogues: Effect of Conformational Constraints on Opiate Receptor Selectivity", J. Med. Chem. 25:1432-1438 (1982).

Majer et al., "Synthesis of Methylated Phenylalanines Via Hydrogenolysis of Corresponding 1, 2, 3, 4 Tetrahydroisoquinoline-3-Caraboxylic Acids,", Int. Journal of Peptide & Protein Research, 43:62-68 (1994).

Schiller et al., "TIPP: A Highly Potent and Stable Pseudopeptide δ Opioid Receptor Antagonist with Extraordinary δ Selectivity", J. Med. Chem. 36:3182-3187 (1993).

Schiller et al., "Unsulfated C-Terminal 7-Peptide of Cholecystokinin: A New Ligand of the Opiate Receptor," Biochemical and Biophysical Research Communications, 85:1332-1338 (1978).

Fuhrman et al., "Oxidative stress increases the expression of the CD36 scavenger receptor and the cellular uptake of oxidized low-density lipoprotein in macrophages from atherosclerotic mice: protective role of antioxidants and of paraoxonase", Atherosclerosis, Mar. 7, 2002, vol. 161, Iss 2, pp. 307-316, entire document.

Herve, et al., "On the Immunogenic Properties of Retro-Inverso Peptides. Total Retro-Inversion of T-Cell Epitopes Causes a Loss of Binding to MHC II Molecules", Molecular Immunology, vol. 34, No. 2, pp. 157-163, 1997.

Guerrini, et al., "Opioid receptor selectivity alteration by single residue replacement: synthesis and activity profile of [Dmt] deltorphin B", European Journal of Pharmacology 302, (1996) 37-42. Abstract only.

James A Wells, "Additivity of Mutational Effects in Proteins", Biochemistry, American Chemical Society, vol. 29, No. 37, Sep. 18, 1990.

Schiller, et al., "Opioid peptide analogs with novel activity profiles as potential therapeutic agents for use in analgesia", Peptide Science-Present and Future, Proc. Int. Pept. Symp., 1st, Y. Shimonishi (ed), 1999, pp. 665-669.

Schiller, et al., "Opioid Peptide Analogs With Novel Activity Profiles as Potential Therapeutic Agents For Use in Analgesia", First International Peptide Symposium, Program & Abstracts, Nov. 30-Dec. 5, 1997, Kyoto, Japan, 0-36, p. 77.

Zhao, et al., "Cell-permeable Peptide Antioxidants Targeted to Inner Mitochondrial Membrane inhibit Mitochondrial Swelling, Oxidative Cell Death, and Reperfusion Injury", J. Biol. Chem., Aug. 2004, vol. 279, No. 33, pp. 34682-34690.

Zhao et al., "Cell-Permeable Peptide Antioxidants Targeted to Inner Mitochondrial Membrane Inhibit Mitochondrial Swelling, Oxidative Cell Death, and Reperfusion Injury", Journal of Biological Chemistry, 279:33, 34682-34690 (Aug. 2004).

* cited by examiner

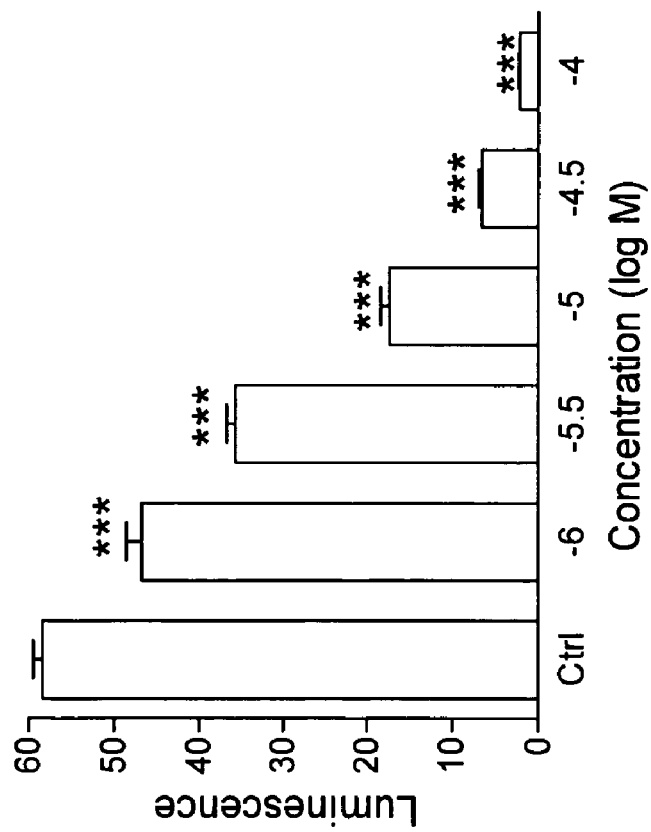
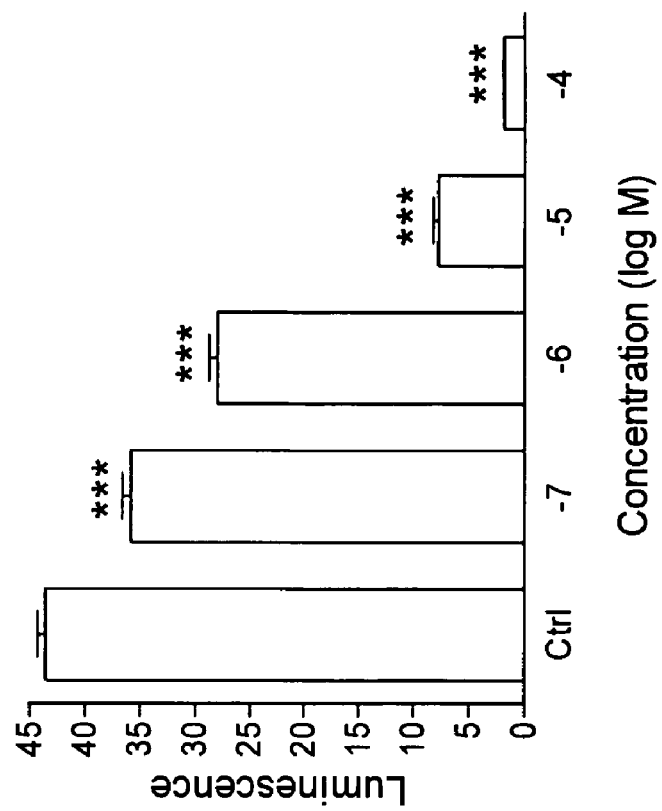
Fig. 1A
Fig. 1B

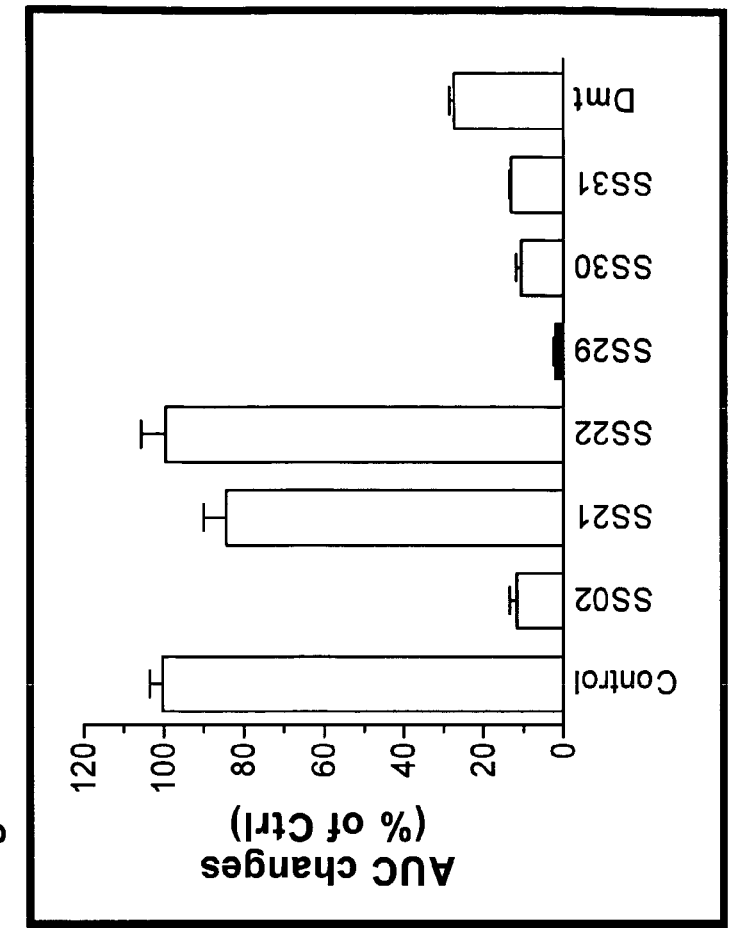
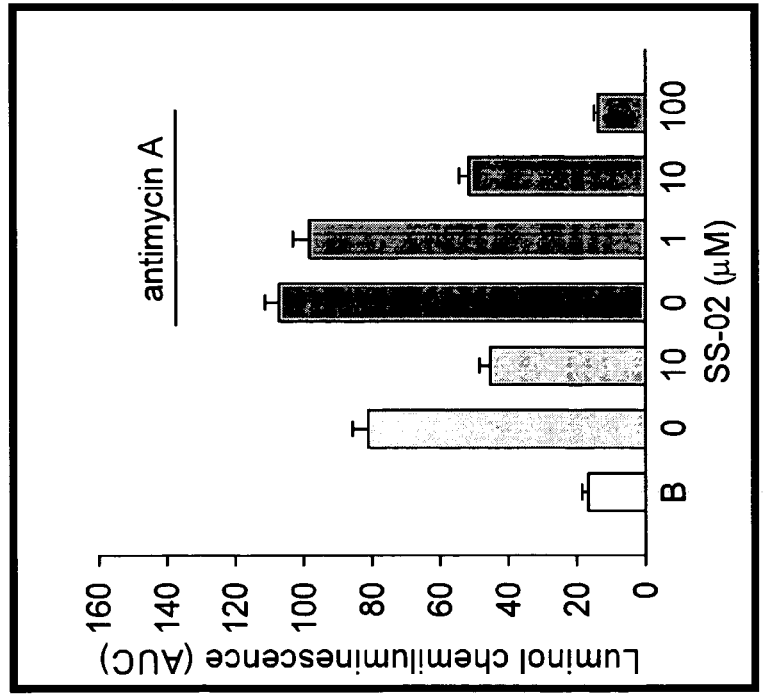
Fig. 4A
Fig. 4B

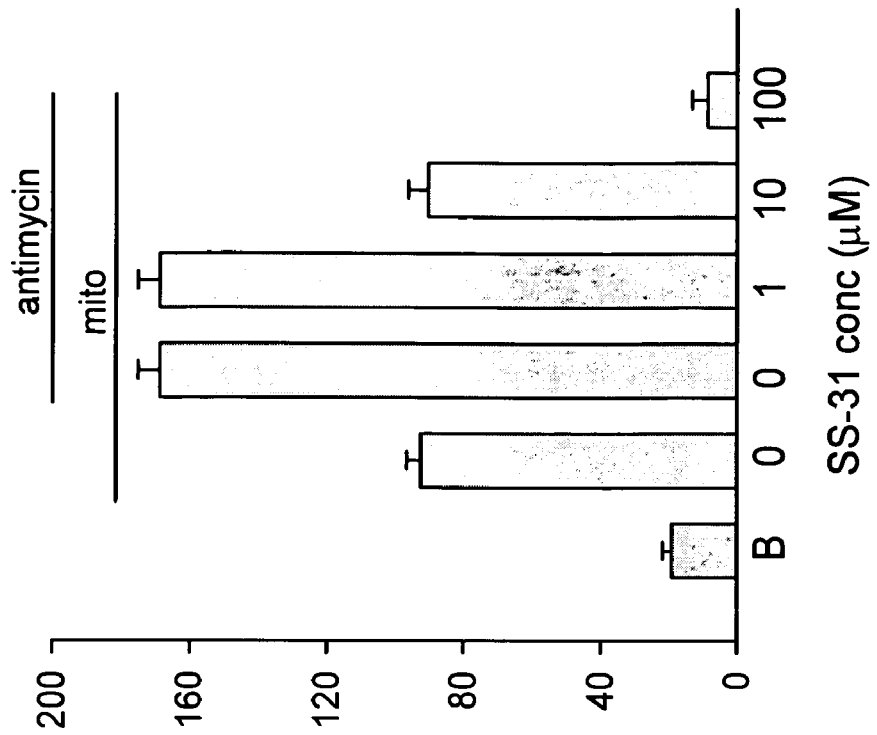
Fig. 5A Spontaneous ROS production
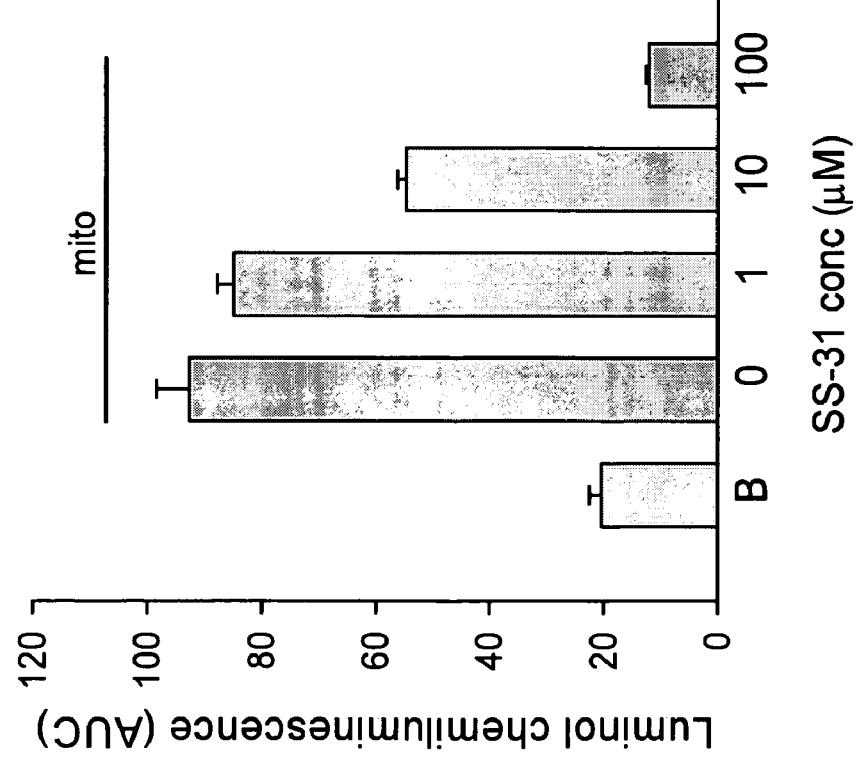
Fig. 5B Antimycin-induced ROS production Fig. 12A1
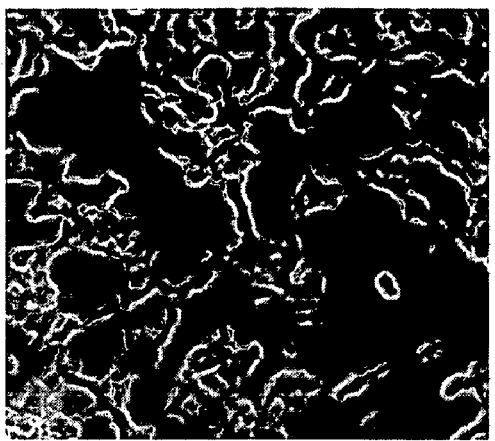
Fig. 12A2
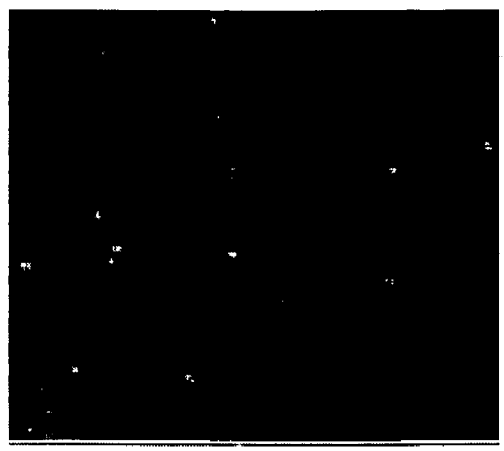
Fig. 12B1
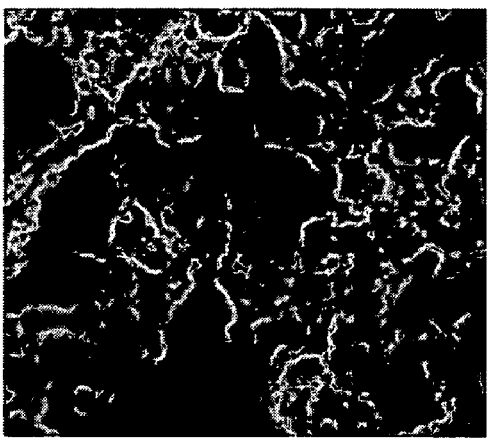
Fig. 12B2
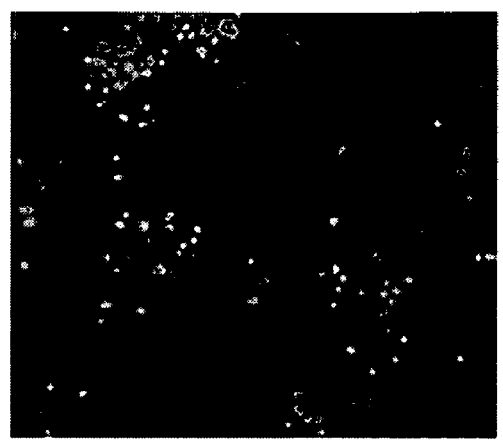
Fig. 12C1
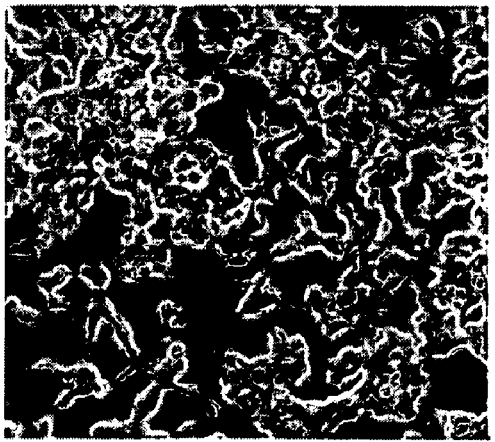
Fig. 12C2
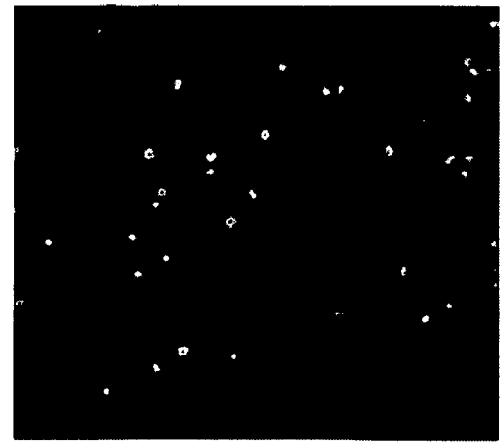

METHODS FOR REDUCING OXIDATIVE DAMAGE

This application asserts priority of U.S. Provisional Application Ser. No. 60/538,841 filed on Jan. 23, 2004. The specification of U.S. Provisional Application Ser. No. 60/538,841 is hereby incorporated by reference in its entirety.

This invention was made with government support from the National Institute on Drug Abuse under Grant No. PO1 DA08924. The U.S. government has certain rights in this invention.

BACKGROUND OF THE INVENTION

Mitochondria are essential to cell survival as the main producers of ATP via oxidative phosphorylation. However, the mitochondria respiratory chain is also a major source of oxidative free radicals. For example, radical production can occur as a result of the reaction of mitochondrial electron carriers, such as ubiquinol, with oxygen to form a superoxide. Superoxides react by dismutation to hydrogen peroxide, which can decompose to hydroxyl radical. In addition, superoxides react with nitric oxide to form peroxynitrite and other reactive oxidants.

Aging is associated not only with increased reactive oxygen species (ROS) production, but also a decrease in the endogenous antioxidant defense mechanisms. Mitochondria are particularly vulnerable to oxidative stress because they are continuously exposed to ROS. As a consequence, mitochondria decay is often associated with aging.

Free radicals, including ROS, and reactive nitrogen species (RNS) produce diverse non-specific damage to biological molecules, including lipids, proteins, RNA and DNA. Such damage of these molecules has been implicated in numerous clinical disorders, such as atherosclerosis, preeclampsia, Alzheimer's disease, Parkinson's disease and arthritis.

Antioxidant therapy can potentially delay the aging process, and be beneficial in a host of human diseases and conditions, such as those described above. However, the development of specific mitochondrial therapies has been hampered by the difficulty of delivering antioxidant molecules to mitochondria in vivo. For example, the molecule must first be taken up across the plasma membrane into the cytoplasm, and then targeted selectively to mitochondria.

None of the currently available antioxidant compounds specifically target mitochondria. The endogenous antioxidants, superoxide dismutase and catalase, are poorly absorbed orally, have short half-lives, and do not cross the blood-brain barrier. The natural antioxidants (e.g., Vitamin E, coenzyme Q, polyphenols) are not water-soluble and tend to accumulate in cell membranes and only cross the blood-brain barrier slowly.

Therefore, there is a need for improved methods of reducing oxidative damage with antioxidative compounds that cross cell membranes. In addition, it would also be beneficial for the antioxidative compounds to specifically target mitochondria.

SUMMARY OF THE INVENTION

These and other objectives have been met by the present invention which provide a method for reducing oxidative damage in a mammal in need thereof. The method comprises administering to the mammal an effective amount of an aromatic cationic peptide. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a is the largest number that is less than or equal to $p_t$+1, except that when a is 1, $p_t$ may also be 1; and (f) at least one tyrosine or tryptophan amino acid.

In another embodiment, the invention also provides a method of reducing oxidative damage in a removed organ of a mammal. The method comprises administering to the removed organ an effective amount of an aromatic-cationic peptide. The aromatic-cationic peptide have (a) at least one net positive charge; (b) a minimum of four amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t$+1, except that when a is 1, $p_t$ may also be 1; and (f) at least one tyrosine or tryptophan amino acid.

In a further embodiment, the invention provides a method of reducing oxidative damage in a mammal in need thereof. The method comprises administering to the mammal an effective amount of an aromatic-cationic peptide. The aromatic-cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t$+1, except that when a is 1, $p_t$ may also be, 1, and (f) at least one tyrosine or tryptophan amino acid.

In yet a further embodiment, the invention provides a method of reducing oxidative damage in a removed organ of a mammal. The method comprises administering to the removed organ an effective amount of an aromatic-cationic peptide. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a is the largest number that is less than or equal to $p_t$+1, except that when a is 1, $p_t$ may also be 1, and (f) at least one tyrosine or tryptophan amino acid.

In yet another embodiment, the invention provides a method of reducing oxidative damage in a cell in need thereof. The aromatic cationic peptide have (a) at least one net positive charge; (b) a minimum of three amino acids; (c) a maximum of about twenty amino acids; (d) a relationship between the minimum number of net positive charges ($p_m$) and the total number of amino acid residues (r) wherein $3p_m$ is the largest number that is less than or equal to r+1; (e) a relationship between the minimum number of aromatic groups (a) and the total number of net positive charges ($p_t$) wherein 3a is the largest number that is less than or equal to $p_t$+1, except that when a is 1, $p_t$ may also be 1, and (f) at least one tyrosine or tryptophan amino acid.

In an additional embodiment, the invention provides a method of reducing oxidative damage in a cell in need thereof. The aromatic cationic peptide have (a) at least one net positive charge; (b) a minimum of three amino acids; (c) a maximum of about twenty amino acids; (d) a relationship between the minimum number of net positive charges (m) and the total number of amino acid residues (r) wherein $3p_m$ is the largest number that is less than or equal to r+1; (e) a relationship between the minimum number of aromatic groups (a) and the total number of net positive charges ($p_t$) wherein 2a is the largest number that is less than or equal to $p_t$+1, except that when a is 1, pt may also be 1, and (f) at least one tyrosine or tryptophan amino acid

BRIEF DESCRIPTION OF THE FIGURES

FIG. 1. (A) SS-02 and (B) SS-05 dose-dependently scavenge $H_2O_2$.

FIG. 4. (A) SS-02 inhibits mitochondrial production of hydrogen peroxide as measured by luminol chemiluminescence under basal conditions and upon stimulation by antimycin. (B) SS-02, SS-29, SS-30 and SS-31 reduced spontaneous generation of hydrogen peroxide generated by isolated mitochondria.

FIG. 5. (A) SS-31 inhibits spontaneous production of hydrogen hydroperoxide by isolated mitochondria and (B) SS-31 inhibits hydrogen peroxide production stimulated by antimycin.

DETAILED DESCRIPTION OF THE INVENTION

Figure 2A:
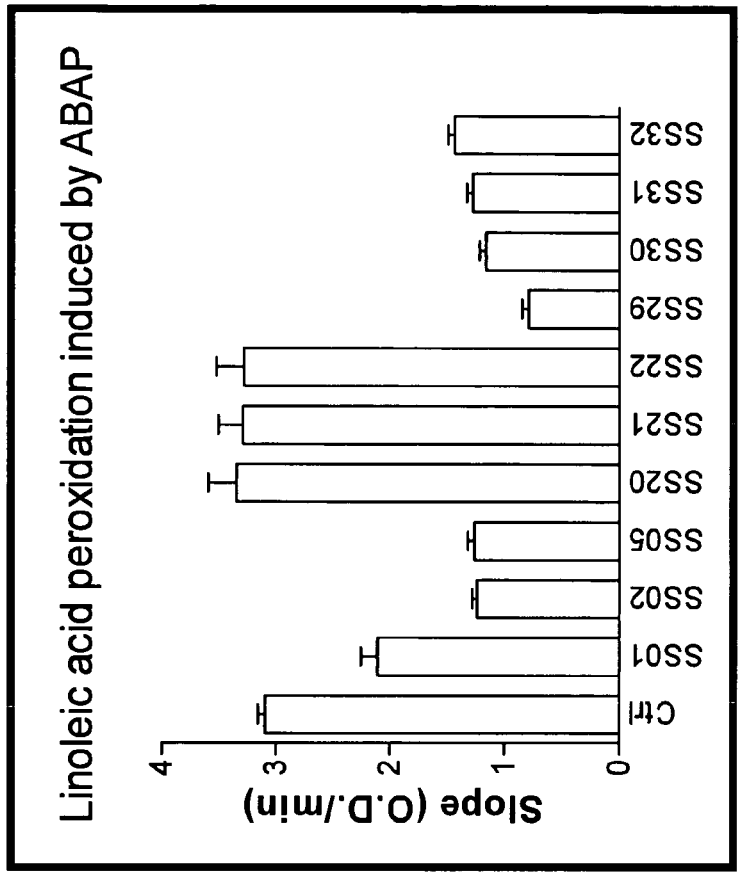
FIG. 2. (A) SS-02 dose-dependently inhibits linoleic acid peroxidation induced by ABAP and (B) SS-02, SS-05, SS-29, SS-30, SS-31, SS-32 and Dmt reduced the rate of linoleic acid peroxidation induced by ABAP.

The invention is based on the surprising discovery by the inventors that certain aromatic-cationic peptides reduce oxidative damage. Reducing oxidative damage is important since free radicals, such as ROS and RNS, produce diverse non-specific damage to lipids, proteins, RNA and DNA. Oxidative damage caused by free radicals is associated with several diseases and conditions in mammals.

Peptides

The aromatic-cationic peptides useful in the present invention are water-soluble and highly polar. Despite these properties, the peptides can readily penetrate cell membranes.

The aromatic-cationic peptides useful in the present invention include a minimum of three amino acids, and preferably include a minimum of four amino acids, covalently joined by peptide bonds.

The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein, the term "amino acid" is used to refer to any organic molecule that contains at least one amino group and at least one carboxyl group. Preferably, at least one amino group is at the α position relative to the carboxyl group.

The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present invention can contain one or more non-naturally occurring amino acids. The non-naturally occurring amino acids may be L-, dextrorotatory (D), or mixtures thereof. Optimally, the peptide has no amino acids that are naturally occurring.

Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases.

The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D- non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids.

If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that at least one of the amino acids present in the aromatic-cationic peptide is a tyrosine or tryptophan residue, or a derivative thereof.

It is also important that the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-Arg (SEQ. ID. NO: 1) has one negatively charged amino acid (i.e., Glu) and four positively charged amino acids (i.e., two Arg residues, one Lys, and one His). Therefore, the above peptide has a net positive charge of three.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

| (r) | | | | | | | | | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-Arg-Phe-Trp (SEQ. ID. NO: 2) has a net positive charge of two (contributed by the lysine and arginine residues) and three aromatic groups (contributed by tyrosine, phenylalanine and tryptophan residues).

In one embodiment of the present invention, the aromatic-cationic peptides useful in the methods of the present invention have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

| | | | | | | | | | | ($p_t$) | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

| | | | | | | | | | | ($p_t$) | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

```
Lys-D-Arg-Tyr-NH2,

D-Tyr-Trp-Lys-NH2,

Trp-D-Lys-Tyr-Arg-NH2,

Tyr-His-D-Gly-Met,

Tyr-D-Arg-Phe-Lys-Glu-NH2,
(SEQ. ID. NO: 3),

Met-Tyr-D-Lys-Phe-Arg,
(SEQ. ID. NO: 4),

D-His-Glu-Lys-Tyr-D-Phe-Arg,
(SEQ. ID. NO: 5),

Lys-D-Gln-Tyr-Arg-D-Phe-Trp-NH2,
(SEQ. ID. NO: 6),

Phe-D-Arg-Lys-Trp-Tyr-D-Arg-His,
(SEQ. ID. NO: 7),

Gly-D-Phe-Lys-Tyr-His-D-Arg-Tyr-NH2,
(SEQ. ID. NO: 8),
```

-continued

```
Val-D-Lys-His-Tyr-D-Phe-Ser-Tyr-Arg-NH2,
(SEQ. ID. NO: 9),

Trp-Lys-Phe-D-Asp-Arg-Tyr-D-His-Lys,
(SEQ. ID. NO: 10),

Lys-Trp-D-Tyr-Arg-Asn-Phe-Tyr-D-His-NH2,
(SEQ. ID. NO: 11),

Thr-Gly-Tyr-Arg-D-His-Phe-Trp-D-His-Lys,
(SEQ. ID. NO: 12),

Asp-D-Trp-Lys-Tyr-D-His-Phe-Arg-D-Gly-Lys-NH2,
(SEQ. ID. NO: 13),

D-His-Lys-Tyr-D-Phe-Glu-D-Asp-D-His-D-Lys-Arg-Trp-NH2,
(SEQ. ID. NO: 14),

Ala-D-Phe-D-Arg-Tyr-Lys-D-Trp-His-D-Tyr-Gly-Phe,
(SEQ. ID. NO: 15),

Tyr-D-His-Phe-D-Arg-Asp-Lys-D-Arg-His-Trp-D-His-Phe,
(SEQ. ID. NO: 16),

Phe-Phe-D-Tyr-Arg-Glu-Asp-D-Lys-Arg-D-Arg-His-Phe-NH2,
(SEQ. ID. NO: 17),

Phe-Tyr-Lys-D-Arg-Trp-His-D-Lys-D-Lys-Glu-Arg-D-Tyr-Thr,
(SEQ. ID. NO: 18),

Tyr-Asp-D-Lys-Tyr-Phe-D-Lys-D-Arg-Phe-Pro-D-Tyr-His-Lys,
(SEQ. ID. NO: 19),

Glu-Arg-D-Lys-Tyr-D-Val-Phe-D-His-Trp-Arg-D-Gly-Tyr-Arg-D-Met-NH2,
(SEQ. ID. NO: 20),

Arg-D-Leu-D-Tyr-Phe-Lys-Glu-D-Lys-Arg-D-Trp-Lys-D-Phe-Tyr-D-Arg-Gly,
(SEQ. ID. NO: 21),

D-Glu-Asp-Lys-D-Arg-D-His-Phe-Phe-D-Val-Tyr-Arg-Tyr-D-Tyr-Arg-His-Phe-NH2,
(SEQ. ID. NO: 22),

Asp-Arg-D-Phe-Cys-Phe-D-Arg-D-Lys-Tyr-Arg-D-Tyr-Trp-D-His-Tyr-D-Phe-Lys-Phe,
(SEQ. ID. NO: 23),

His-Tyr-D-Arg-Trp-Lys-Phe-D-Asp-Ala-Arg-Cys-D-Tyr-His-Phe-D-Lys-Tyr-His-Ser-NH2,
(SEQ. ID. NO: 24),

Gly-Ala-Lys-Phe-D-Lys-Glu-Arg-Tyr-His-D-Arg-D-Arg-Asp-Tyr-Trp-D-His-Trp-His-D-Lys-Asp,
(SEQ. ID. NO: 25), and Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH2.
(SEQ. ID. NO: 26).
```

In one embodiment, the peptides useful in the methods of the present invention have mu-opioid receptor agonist activity (i.e., activate the mu-opioid receptor). Activation of the mu-opioid receptor typically elicits an analgesic effect.

In certain instances, an aromatic-cationic peptide having mu-opioid receptor activity is preferred. For example, during short-term treatment, such as in an acute disease or condition, it may be beneficial to use an aromatic-cationic peptide that activates the mu-opioid receptor. For example, the acute diseases and conditions can be associated with moderate or severe pain. In these instances, the analgesic effect of the aromatic-cationic peptide may be beneficial in the treatment regimen of the patient or other mammal, although an aromatic-cationic peptide which does not activate the mu-opioid receptor may also be used with or without an analgesic according to clinical requirements.

Alternatively, in other instances, an aromatic-cationic peptide that does not have mu-opioid receptor activity is preferred. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal.

Potential adverse effects may include sedation, constipation, nervous system depression and respiratory depression. In such instances an aromatic-cationic peptide that does not activate the mu-opioid receptor may be an appropriate treatment.

Examples of acute conditions include heart attack, stroke and traumatic injury. Traumatic injury may include traumatic brain and spinal cord injury.

Examples of chronic diseases or conditions include coronary artery disease and any neurodegenerative disorders, such as those described below.

Peptides useful in the methods of the present invention which have mu-opioid receptor activity are typically those peptides which have a tyrosine residue or a tyrosine derivative at the N-terminus (i.e., the first amino acid position). Preferred derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltryosine (Hmt).

In a particular preferred embodiment, a peptide that has mu-opioid receptor activity has the formula Tyr-D-Arg-Phe-Lys-NH$_2$ (for convenience represented by the acronym: DALDA, which is referred to herein as SS-01). DALDA has a net positive charge of three, contributed by the amino acids tyrosine, arginine, and lysine and has two aromatic groups contributed by the amino acids phenylalanine and tyrosine. The tyrosine of DALDA can be a modified derivative of tyrosine such as in 2',6'-dimethyltyrosine to produce the compound having the formula 2',6'-Dmt-D-Arg-Phe-Lys-NH$_2$ (i.e., Dmt$^1$-DALDA, which is referred to herein as SS-02).

Peptides that do not have mu-opioid receptor activity generally do not have a tyrosine residue or a derivative of tyrosine at the N-terminus (i.e., amino acid position one). The amino acid at the N-terminus can be any naturally occurring or non-naturally occurring amino acid other than tyrosine.

In one embodiment, the amino acid at the N-terminus is phenylalanine or its derivative. Preferred derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp). In another preferred embodiment, the amino acid residue at the N-terminus is arginine. An example of such a peptide is D-Arg-2'6'Dmt-Lys-Phe-NH$_2$ (referred to in this specification as SS-31).

Another aromatic-cationic peptide that does not have mu-opioid receptor activity has the formula Phe-D-Arg-Dmt-Lys-NH$_2$. Alternatively, the N-terminal phenylalanine can be a derivative of phenylalanine such as 2',6'-dimethylphenylalanine (2'6'Dmp). DALDA containing 2',6'-dimethylphenylalanine at amino acid position one has the formula 2',6'-Dmp-D-Arg-Dmt-Lys-NH$_2$.

In a preferred embodiment, the amino acid sequence of Dmt$^1$-DALDA (SS-02) is rearranged such that Dmt is not at the N-terminus. An example of such an aromatic-cationic peptide that does not have mu-opioid receptor activity has the formula D-Arg-2'6'Dmt-Lys-Phe-NH$_2$ (SS-31).

DALDA, SS-31, and their derivatives can further include functional analogs. A peptide is considered a functional analog of DALDA or SS-31 if the analog has the same function as DALDA or SS-31. The analog may, for example, be a substitution variant of DALDA or SS-31, wherein one or more amino acid is substituted by another amino acid.

Suitable substitution variants of DALDA or SS-31 include conservative amino acid substitutions. Amino acids may be grouped according to their physicochemical characteristics as follows:

(a) Non-polar amino acids: Ala(A) Ser(S) Thr(T) Pro(P) Gly(G);

(b) Acidic amino acids: Asn(N) Asp(D) Glu(E) Gln(O);

(c) Basic amino acids: His(H) Arg(R) Lys(K);

(d) Hydrophobic amino acids: Met(M) Leu(L) Ile(I) Val (V); and (e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of analogs useful in the practice of the present invention that activate mu-opioid receptors include, but are not limited to, the aromatic-cationic peptides shown in Table 1.

TABLE 1

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| 2'6'Dmt | D-Arg | Phe | Lys | | NH$_2$ |
| 2'6'Dmt | D-Arg | Phe | Lys | Cys | NH$_2$ (SEQ. ID. NO: 27) |
| 2'6'Dmt | D-Arg | Phe | Lys-NH(CH$_2$)$_2$—NH-dns | | NH$_2$ |
| 2'6'Dmt | D-Arg | Phe | Lys-NH(CH$_2$)$_2$—NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Ahp | | NH$_2$ |
| 2'6'Dmt | D-Arg | Phe | Orn | | NH$_2$ |
| 2'6'Dmt | D-Arg | Phe | Dab | | NH$_2$ |
| 2'6'Dmt | D-Arg | Phe | Dap | | NH$_2$ |
| 2'6'Dmt | D-Arg | Phe | Ahp(2-aminoheptanoic acid) | | NH$_2$ |
| Bio-2'6'Dmt | D-Arg | Phe | Lys | | NH$_2$ |
| 3'5'Dmt | D-Arg | Phe | Lys | | NH$_2$ |
| 3'5'Dmt | D-Arg | Phe | Orn | | NH$_2$ |
| 3'5'Dmt | D-Arg | Phe | Dab | | NH$_2$ |
| 3'5'Dmt | D-Arg | Phe | Dap | | NH$_2$ |
| Tyr | D-Arg | Tyr | Lys | | NH$_2$ |
| Tyr | D-Arg | Tyr | Orn | | NH$_2$ |
| Tyr | D-Arg | Tyr | Dab | | NH$_2$ |
| Tyr | D-Arg | Tyr | Dap | | NH$_2$ |
| 2'6'Dmt | D-Arg | Tyr | Lys | | NH$_2$ |
| 2'6'Dmt | D-Arg | Tyr | Orn | | NH$_2$ |
| 2'6'Dmt | D-Arg | Tyr | Dab | | NH$_2$ |
| 2'6'Dmt | D-Arg | Tyr | Dap | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 2'6'Dmt | D-Arg | 2'6'Dmt | Lys | | NH$_2$ |
| 2'6'Dmt | D-Arg | 2'6'Dmt | Orn | | NH$_2$ |
| 2'6'Dmt | D-Arg | 2'6'Dmt | Dab | | NH$_2$ |
| 2'6'Dmt | D-Arg | 2'6'Dmt | Dap | | NH$_2$ |
| 3'5'Dmt | D-Arg | 3'5'Dmt | Arg | | NH$_2$ |
| 3'5'Dmt | D-Arg | 3'5'Dmt | Lys | | NH$_2$ |
| 3'5'Dmt | D-Arg | 3'5'Dmt | Orn | | NH$_2$ |
| 3'5'Dmt | D-Arg | 3'5'Dmt | Dab | | NH$_2$ |
| Tyr | D-Lys | Phe | Dap | | NH$_2$ |
| Tyr | D-Lys | Phe | Arg | | NH$_2$ |
| Tyr | D-Lys | Phe | Lys | | NH$_2$ |
| Tyr | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | Phe | Arg | | NH$_2$ |
| 2'6'Dmt | D-Lys | Phe | Lys | | NH$_2$ |
| 3'5'Dmt | D-Lys | Phe | Orn | | NH$_2$ |
| 3'5'Dmt | D-Lys | Phe | Dab | | NH$_2$ |
| 3'5'Dmt | D-Lys | Phe | Dap | | NH$_2$ |
| 3'5'Dmt | D-Lys | Phe | Arg | | NH$_2$ |
| Tyr | D-Lys | Tyr | Lys | | NH$_2$ |
| Tyr | D-Lys | Tyr | Orn | | NH$_2$ |
| Tyr | D-Lys | Tyr | Dab | | NH$_2$ |
| Tyr | D-Lys | Tyr | Dap | | NH$_2$ |
| 2'6'Dmt | D-Lys | Tyr | Lys | | NH$_2$ |
| 2'6'Dmt | D-Lys | Tyr | Orn | | NH$_2$ |
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |
| 3'5'Dmt | D-Lys | Phe | Arg | | NH$_2$ |
| 3'5'Dmt | D-Orn | Phe | Arg | | NH$_2$ |
| Tyr | D-Lys | Tyr | Arg | | NH$_2$ |
| Tyr | D-Orn | Tyr | Arg | | NH$_2$ |
| Tyr | D-Dab | Tyr | Arg | | NH$_2$ |
| Tyr | D-Dap | Tyr | Arg | | NH$_2$ |
| 2'6'Dmt | D-Arg | 2'6'Dmt | Arg | | NH$_2$ |
| 2'6'Dmt | D-Lys | 2'6'Dmt | Arg | | NH$_2$ |
| 2'6'Dmt | D-Orn | 2'6'Dmt | Arg | | NH$_2$ |
| 2'6'Dmt | D-Dab | 2'6'Dmt | Arg | | NH$_2$ |
| 3'5'Dmt | D-Dap | 3'5'Dmt | Arg | | NH$_2$ |
| 3'5'Dmt | D-Arg | 3'5'Dmt | Arg | | NH$_2$ |
| 3'5'Dmt | D-Lys | 3'5'Dmt | Arg | | NH$_2$ |
| 3'5'Dmt | D-Orn | 3'5'Dmt | Arg | | NH$_2$ |
| Mmt | D-Arg | Phe | Lys | | NH$_2$ |
| Mmt | D-Arg | Phe | Orn | | NH$_2$ |
| Mmt | D-Arg | Phe | Dab | | NH$_2$ |
| Mmt | D-Arg | Phe | Dap | | NH$_2$ |
| Tmt | D-Arg | Phe | Lys | | NH$_2$ |
| Tmt | D-Arg | Phe | Orn | | NH$_2$ |
| Tmt | D-Arg | Phe | Dab | | NH$_2$ |
| Tmt | D-Arg | Phe | Dap | | NH$_2$ |
| Hmt | D-Arg | Phe | Lys | | NH$_2$ |
| Hmt | D-Arg | Phe | Orn | | NH$_2$ |
| Hmt | D-Arg | Phe | Dab | | NH$_2$ |
| Hmt | D-Arg | Phe | Dap | | NH$_2$ |
| Mmt | D-Lys | Phe | Lys | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Mmt | D-Lys | Phe | Orn | | $NH_2$ |
| Mmt | D-Lys | Phe | Dab | | $NH_2$ |
| Mmt | D-Lys | Phe | Dap | | $NH_2$ |
| Mmt | D-Lys | Phe | Arg | | $NH_2$ |
| Tmt | D-Lys | Phe | Lys | | $NH_2$ |
| Tmt | D-Lys | Phe | Orn | | $NH_2$ |
| Tmt | D-Lys | Phe | Dab | | $NH_2$ |
| Tmt | D-Lys | Phe | Dap | | $NH_2$ |
| Tmt | D-Lys | Phe | Arg | | $NH_2$ |
| Hmt | D-Lys | Phe | Lys | | $NH_2$ |
| Hmt | D-Lys | Phe | Orn | | $NH_2$ |
| Hmt | D-Lys | Phe | Dab | | $NH_2$ |
| Hmt | D-Lys | Phe | Dap | | $NH_2$ |
| Hmt | D-Lys | Phe | Arg | | $NH_2$ |
| Mmt | D-Lys | Phe | Arg | | $NH_2$ |
| Mmt | D-Orn | Phe | Arg | | $NH_2$ |
| Mmt | D-Dab | Phe | Arg | | $NH_2$ |
| Mmt | D-Dap | Phe | Arg | | $NH_2$ |
| Mmt | D-Arg | Phe | Arg | | $NH_2$ |
| Tmt | D-Lys | Phe | Arg | | $NH_2$ |
| Tmt | D-Orn | Phe | Arg | | $NH_2$ |
| Tmt | D-Dab | Phe | Arg | | $NH_2$ |
| Tmt | D-Dap | Phe | Arg | | $NH_2$ |
| Tmt | D-Arg | Phe | Arg | | $NH_2$ |
| Hmt | D-Lys | Phe | Arg | | $NH_2$ |
| Hmt | D-Orn | Phe | Arg | | $NH_2$ |
| Hmt | D-Dab | Phe | Arg | | $NH_2$ |
| Hmt | D-Dap | Phe | Arg | | $NH_2$ |
| Hmt | D-Arg | Phe | Arg | | $NH_2$ |

Dab = diaminobutyric acid
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of analogs useful in the practice of the present invention that do not activate mu-opioid receptors include, but are not limited to, the aromatic-cationic peptides shown in Table 2.

TABLE 2

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |

The amino acids of the peptides shown in table 1 and 2 may be in either the L- or the D-configuration.

Methods of Reducing Oxidative Damage

The peptides described above are useful in reducing oxidative damage in a mammal in need thereof. Mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO.), superoxide anion radical ($O_2 \cdot^-$), nitric oxide (NO·), hydrogen peroxide ($H_2O_2$), hypochlorous acid (HOCl) and peroxynitrite anion ($ONOO^-$).

In one embodiment, a mammal in need thereof may be a mammal undergoing a treatment associated with oxidative damage. For example, the mammal may be undergoing reperfusion. Reperfusion refers to the restoration of blood flow to any organ or tissue in which the flow of blood is decreased or blocked. The restoration of blood flow during reperfusion leads to respiratory burst and formation of free radicals.

Decreased or blocked blood flow may be due to hypoxia or ischemia. The loss or severe reduction in blood supply during hypoxia or ischemia may, for example, be due to thromboembolic stroke, coronary atherosclerosis, or peripheral vascular disease.

Numerous organs and tissues are subject to ischemia or hypoxia. Examples of such organs include brain, heart, kidney, intestine and prostate. The tissue affected is typically muscle, such as cardiac, skeletal, or smooth muscle. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

The restoration of blood flow (reperfusion) can occur by any method known to those in the art. For instance, reperfusion of ischemic cardiac tissues may arise from angioplasty, coronary artery bypass graft, or the use of thrombolytic drugs. Reducing oxidative damage associated with ischemia/hypoxia and reperfusion is important because the tissue damage associated with ischemia/hypoxia and reperfusion is associated with, for example, myocardial infarction, stroke and hemorrhagic shock.

In another embodiment, a mammal in need thereof can be a mammal with a disease or condition associated with oxidative damage. The oxidative damage can occur in any cell, tissue or organ of the mammal. Examples of cells, tissues or organs include, but are not limited to, endothelial cells, epithelial cells, nervous system cells, skin, heart, lung, kidney and liver. For example, lipid peroxidation and an inflammatory process are associated with oxidative damage for a disease or condition.

Lipid peroxidation refers to oxidative modification of lipids. The lipids can be present in the membrane of a cell. This modification of membrane lipids typically results in change and/or damage to the membrane function of a cell. In addition, lipid peroxidation can also occur in lipids or lipoproteins exogenous of a cell. For example, low-density lipoproteins are susceptible to lipid peroxidation. An example of a condition associated with lipid peroxidation is atherosclerosis. Reducing oxidative damage associated with atherosclerosis is important since atherosclerosis is implicated in, for example, heart attacks and coronary artery disease.

Inflammatory process refers to the activation of the immune system. Typically, the immune system is activated by an antigenic substance. The antigenic substance can be any substance recognized by the immune system, and include self-derived particles and foreign-derived particles. Examples of diseases or conditions occurring from an inflammatory process to self-derived particles include arthritis and multiple sclerosis. Examples of foreign particles include viruses and bacteria.

The virus can be any virus which activates an inflammatory process, and associated with oxidative damage. Examples of viruses include, hepatitis A, B or C virus, human immunodeficiency virus, influenza virus, and bovine diarrhea virus. For example, hepatitis virus can elicit an inflammatory process and formation of free radicals, thereby damaging the liver.

The bacteria can be any bacteria, and include gram-negative or gram-positive bacteria. Gram-negative bacteria contain lipopolysaccharide in the bacteria wall. Examples of gram-negative bacteria include *Escherichia coli, Klebsiella pneumoniae, Proteus* species, *Pseudomonas aeruginosa, Serratia,* and *Bacteroides*. Examples of gram-positive bacteria include pneumococci and streptococci.

An example of an inflammatory process associated with oxidative stress caused by a bacteria is sepsis. Typically, sepsis occurs when gram-negative bacteria enter the bloodstream.

Liver damage caused by a toxic agent is another condition associated with an inflammatory process and oxidative stress. The toxic agent can be any agent which causes damage to the liver. For example, the toxic agent can cause apoptosis and/or necrosis of liver cells. Examples of such agents include alcohol, and medication, such as prescription and non-prescription drugs taken to treat a disease or condition.

The methods of the present invention can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes and microglia.

The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid β-protein. Examples of chronic neurodegenerative diseases associated with damage by free radicals include Parkinson's disease, Alzheimer's disease, Huntington's disease and Amyotrophic Lateral Sclerosis (also known as Lou Gherig's disease).

Other conditions which can be treated in accordance with the present invention include preeclampsia, diabetes, and symptoms of and conditions associated with aging, such as macular degeneration, wrinkles.

In another embodiment, the peptides useful in the present invention may also be used in reducing oxidative damage in an organ of a mammal prior to transplantation. For example, a removed organ, when subjected to reperfusion after transplantation can be susceptible to oxidative damage. Therefore, the peptides can be used to reduce oxidative damage from reperfusion of the transplanted organ.

The removed organ can be any organ suitable for transplantation. Examples of such organs include, the heart, liver, kidney, lung, and pancreatic islets. The removed organ is placed in a suitable medium, such as in a standard buffered solution commonly used in the art.

For example, a removed heart can be placed in a cardioplegic solution containing the peptides described above. The concentration of peptides in the standard buffered solution can be easily determined by those skilled in the art. Such concentrations may be, for example, between about 0.01 nM to about 10 μM, preferably about 0.1 nM to about 10 μM, more preferably about 1 µM to about 5 µM, and even more preferably about 1 nM to about 100 nM.

In yet another embodiment, the invention provides a method for reducing oxidative damage in a cell in need thereof. Cells in need of reducing oxidative damage are generally those cells in which the cell membrane or DNA of the cell has been damaged by free radicals, for example, ROS and/or RNS. Examples of cells capable of being subjected to oxidative damage include the cells described herein. Suitable examples of cells include pancreatic islet cells, myocytes, endothelial cells, neuronal cells, stem cells, etc.

The cells can be tissue culture cells. Alternatively, the cells may be obtained from a mammal. In one instance, the cells can be damaged by oxidative damage as a result of an insult. Such insults include, for example, a disease or condition (e.g., diabetes, etc) or ultraviolet radiation (e.g., sun, etc.). For example, pancreatic islet cells damaged by oxidative damage as a result of diabetes can be obtained from a mammal.

The peptides described above can be administered to the cells by any method known to those skilled in the art. For example, the peptides can be incubated with the cells under suitable conditions. Such conditions can be readily determined by those skilled in the art.

Due to reduction of oxidative damage, the treated cells may be capable of regenerating. Such regenerated cells may be administered back into the mammal as a therapeutic treatment for a disease or condition. As mentioned above, one such condition is diabetes.

Oxidative damage is considered to be "reduced" if the amount of oxidative damage in a mammal, a removed organ, or a cell is decreased after administration of an effective amount of the aromatic cationic peptides described above. Typically, the oxidative damage is considered to be reduced if the oxidative damage is decreased by at least about 10%, preferably at least about 25%, more preferably at least about 50%, even more preferably at least about 75%, and most preferably at least about 90%.

Synthesis of the Peptides

The peptides useful in the methods of the present invention may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis," Methods Enzymol. 289, Academic Press, Inc, New York (1997).

Modes of Administration

The peptide useful in the methods of the present invention is administered to a mammal in an amount effective in reducing oxidative damage. The effective amount is determined during pre-clinical trials and clinical trials by methods familiar to physicians and clinicians.

An effective amount of a peptide useful in the methods of the present invention, preferably in a pharmaceutical composition, may be administered to a mammal in need thereof by any of a number of well-known methods for administering pharmaceutical compounds.

The peptide may be administered systemically or locally. In one embodiment, the peptide is administered intravenously. For example, the aromatic-cationic peptides useful in the methods of the present invention may be administered via rapid intravenous bolus injection. Preferably, however, the peptide is administered as a constant rate intravenous infusion.

The peptide can be injected directly into coronary artery during, for example, angioplasty or coronary bypass surgery, or applied onto coronary stents.

The peptide may also be administered orally, topically, intranasally, intramuscularly, subcutaneously, or transdermally. In a preferred embodiment, transdermal administration of the aromatic-cationic peptides by methods of the present invention is by iontophoresis, in which the charged peptide is delivered across the skin by an electric current.

Other routes of administration include intracerebroventricularly or intrathecally. Intracerebroventiculatly refers to administration into the ventricular system of the brain. Intrathecally refers to administration into the space under the arachnoid membrane of the spinal cord. Thus intracerebroventricular or intrathecal administration may be preferred for those diseases and conditions which affect the organs or tissues of the central nervous system. In a preferred embodiment, intrathecal administration is used for traumatic spinal cord injury.

The peptides useful in the methods of the invention may also be administered to mammals by sustained release, as is known in the art. Sustained release administration is a method of drug delivery to achieve a certain level of the drug over a particular period of time. The level typically is measured by serum or plasma concentration.

A description of methods for delivering a compound by controlled release can be found in PCT Application No. WO 02/083106. The PCT application is incorporated herein by reference in its entirety.

Any formulation known in the art of pharmacy is suitable for administration of the aromatic-cationic peptides useful in the methods of the present invention. For oral administration, liquid or solid formulations may be used. Some examples of formulations include tablets, gelatin capsules, pills, troches, elixirs, suspensions, syrups, wafers, chewing gum and the like. The peptides can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides useful in the methods of the present inventions may utilize conventional diluents, carriers, or excipients etc., such as are known in the art can be employed to deliver the peptides. For example, the formulations may comprise one or more of the following: a stabilizer, a surfactant, preferably a nonionic surfactant, and optionally a salt and/or a buffering agent. The peptide may be delivered in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the peptide.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The formulations of the peptides useful in the methods of the present invention may additionally contain one or more conventional additive. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal treated in accordance with the invention can be any mammal, including, for example, farm animals, such as sheep, pigs, cows, and horses; pet animals, such as dogs and cats; laboratory animals, such as rats, mice and rabbits. In a preferred embodiment, the mammal is a human.

EXAMPLES

Example 1

[Dmt$^1$]DALDA Penetrates Cell Membrane

The cellular uptake of [$^3$H][Dmt$^1$]DALDA was studied using a human intestinal epithelial cell line (Caco-2), and confirmed with SH-SY5Y (human neuroblastoma cell), HEK293 (human embryonic kidney cell) and CRFK cells (kidney epithelial cell). Monolayers of cells were grown on 12-well plates ($5\times10^5$ cells/well) coated with collagen for 3 days. On day 4, cells were washed twice with pre-warmed HBSS, and then incubated with 0.2 ml of HBSS containing either 250 nM [$^3$H][Dmt$^1$]DALDA at 37° C. or 4° C. for various times up to 1 h.

[$^3$H][Dmt$^1$]DALDA was observed in cell lysate as early as 5 min, and steady state levels were achieved by 30 min. The total amount of [$^3$H][Dmt$^1$]DALDA recovered in the cell lysate after 1 h incubation represented about 1% of the total drug. The uptake of [$^3$H][Dmt$^1$]DALDA was slower at 4° C. compared to 37° C., but reached 76.5% by 45 min and 86.3% by 1 h. The internalization of [$^3$H][Dmt$^1$]DALDA was not limited to Caco-2 cells, but was also observed in SH-SY5Y, HEK293 and CRFK cells. The intracellular concentration of [Dmt$^1$]DALDA was estimated to be approximately 50 times higher than extracellular concentration.

In a separate experiment, cells were incubated with a range of [Dmt$^1$]DALDA concentrations (1 μM-3 mM) for 1 h at 37° C. At the end of the incubation period, cells were washed 4 times with HBSS, and 0.2 ml of 0.1N NaOH with 1% SDS was added to each well. The cell contents were then transferred to scintillation vials and radioactivity counted. To distinguish between internalized radioactivity from surface-associated radioactivity, an acid-wash step was included. Prior to cell lysis, cells were incubated with 0.2 ml of 0.2 M acetic acid/0.05 M NaCl for 5 min on ice.

The uptake of [Dmt$^1$]DALDA into Caco-2 cells was confirmed by confocal laser scanning microscopy (CLSM) using a fluorescent analog of [Dmt$^1$]DALDA (Dmt-D-Arg-Phe-dnsDap-NH$_2$; where dnsDap=β-dansyl-1-α,β-diaminopropionic acid). Cells were grown as described above and were plated on (35 mm) glass bottom dishes (MatTek Corp., Ashland, Mass.) for 2 days. The medium was then removed and cells were incubated with 1 ml of HBSS containing 0.1 μM to 1.0 μM of the fluorescent peptide analog at 37° C. for 1 h. Cells were then washed three times with ice-cold HBSS and covered with 200 μl of PBS, and microscopy was performed within 10 min at room temperature using a Nikon confocal laser scanning microscope with a C-Apochromat 63×/1.2W corr objective. Excitation was performed at 340 nm by means of a UV laser, and emission was measured at 520 nm. For optical sectioning in z-direction, 5-10 frames with 2.0 μm were made.

CLSM confirmed the uptake of fluorescent Dmt-D-Arg-Phe-dnsDap-NH$_2$ into Caco-2 cells after incubation with 0.1 μM [Dmt$^1$,DnsDap$^4$]DALDA for 1 h at 37° C. The uptake of the fluorescent peptide was similar at 37° C. and 4° C. The fluorescence appeared diffuse throughout the cytoplasm but was completely excluded from the nucleus.

Example 2

Targeting of [Dmt$^1$]DALDA to Mitochondria

To examine the subcellular distribution of [Dmt$^1$]DALDA, the fluorescent analog, [Dmt$^1$,AtnDap$^4$]DALDA (Dmt-D-Arg-Phe-atnDap-NH$_2$; where atn=β-anthraniloyl-1-α,β-diamino-propionic acid), was prepared. The analog contained β-anthraniloyl-1-α,β-diaminopropionic acid in place of the lysine reside at position 4. The cells were grown as described in Example 1 and were plated on (35 mm) glass bottom dishes (MatTek Corp., Ashland, Mass.) for 2 days. The medium was then removed and cells were incubated with 1 ml of HBSS containing 0.1 μM of [Dmt$^1$,AtnDap$^4$]DALDA at 37° C. for 15 min to 1 h.

Cells were also incubated with tetramethylrhodamine methyl ester (TMRM, 25 nM), a dye for staining mitochondria, for 15 min at 37° C. Cells were then washed three times with ice-cold HBSS and covered with 200 μl of PBS, and microscopy was performed within 10 min at room temperature using a Nikon confocal laser scanning microscope with a C-Apochromat 63×/1.2W corr objective.

For [Dmt$^1$,AtnDap$^4$]DALDA, excitation was performed at 350 nm by means of a UV laser, and emission was measured at 520 nm. For TMRM, excitation was performed at 536 nm, and emission was measured at 560 nm.

CLSM showed the uptake of fluorescent [Dmt$^1$,AtnDap$^4$]DALDA into Caco-2 cells after incubation for as little as 15 min at 37° C. The uptake of dye was completely excluded from the nucleus, but the blue dye showed a streaky distribution within the cytoplasm. Mitochondria were labeled red with TMRM. The distribution of [Dmt$^1$,AtnDap$^4$]DALDA to mitochondria was demonstrated by the overlap of the [Dmt$^1$,AtnDap$^4$]DALDA distribution and the TMRM distribution.

Example 3

Scavenging of Hydrogen Peroxide by SS-02 and SS-05 (FIG. 1)

Effect of SS-02 and SS-05 (Dmt-D-Arg-Phe Orn-NH$_2$) on H$_2$O$_2$ as measured by luminol-induced chemiluminescence. 25 μM luminol and 0.7 IU horseradish peroxidase were added to the solution of H$_2$O$_2$ (4.4 nmol) and peptide, and chemiluminescence was monitored with a Chronolog Model 560 aggregometer (Havertown, Pa.) for 20 min at 37° C.

Results show that SS-02 and SS-05 dose-dependently inhibited the luminol response suggesting that these peptides can scavenge H$_2$O$_2$.

Example 4

Figure 2B:
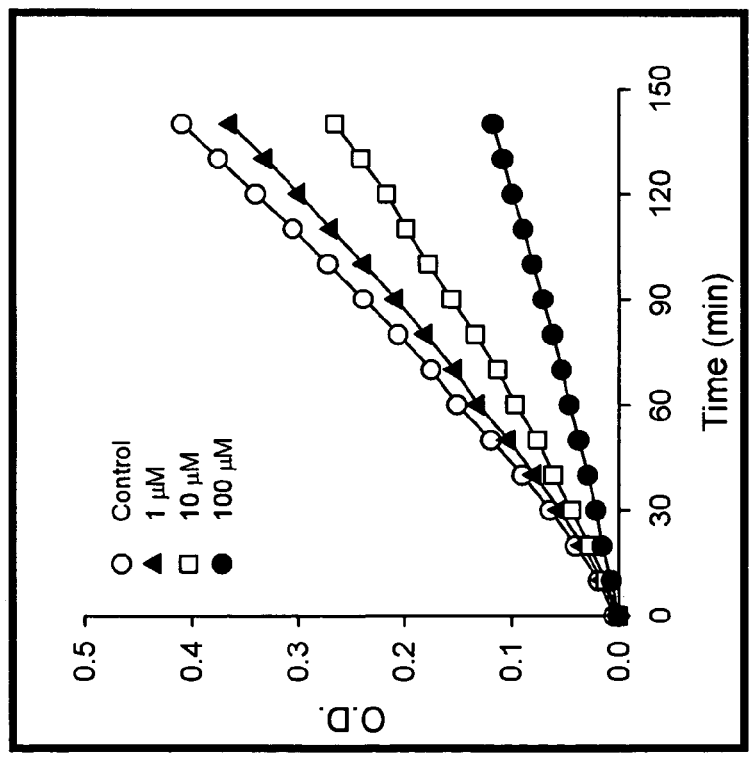

Inhibition of Lipid Peroxidation (FIG. 2)

Linoleic acid peroxidation was induced by a water-soluble initiator, ABAP (2,2'-azobis(2-amidinopropane)), and lipid peroxidation was detected by the formation of conjugated dienes, monitored spectrophotometrically at 236 nm (B. Longoni, W. A. Pryor, P. Marchiafava, *Biochem. Biophys. Res. Commun.* 233, 778-780 (1997)).

5 ml of 0.5 M ABAP and varying concentrations of SS-02 were incubated in 2.4 ml linoleic acid suspension until autoxidation rate became constant. Results show that SS-02 dose-dependently inhibited the peroxidation of linoleic acid.

Various peptides were added in concentration of 100 µM. The data are presented as the slope of diene formation. With the exception of SS-20 (Phe-D-Arg-Phe-Lys-$NH_2$), SS-21 (Cyclohexyl-D-Arg-Phe-Lys-$NH_2$) and SS-22 (Ala-D-Arg-Phe-Lys-$NH_2$), all other SS peptides reduced the rate of linoleic acid peroxidation. Note that SS-20, SS-21 and SS-22 do not contain either tyrosine or dimethyltyrosine residues. SS-01, which contains Tyr rather than Dmt is not as effective in preventing linoleic acid peroxidation. SS-29 is Dmt-D-Cit-Phe Lys-$NH_2$, SS-30 is Phe-D-Arg-Dmt-Lys-$NH_2$, SS-32 is Dmt-D-Arg-Phe-Ahp(2-aminoheptanoic acid)-$NH_2$.

Example 5

Figure 3B:
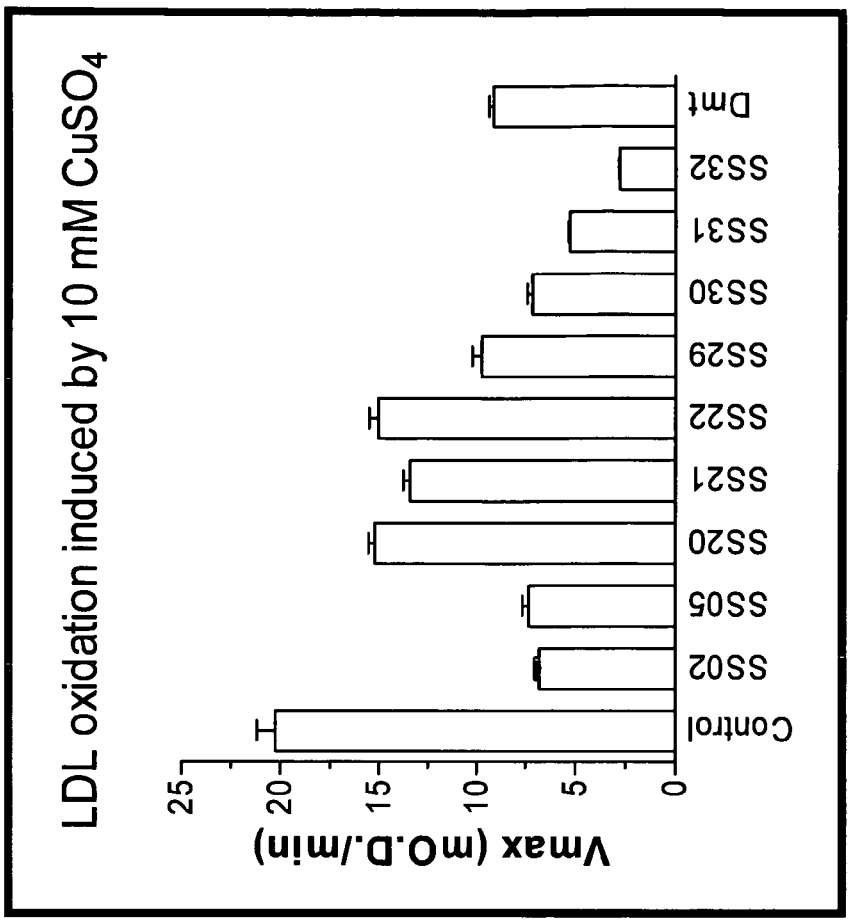
FIG. 3. (A) SS-02 dose-dependently inhibits LDL oxidation induced by 10 mM $CuSO_4$ and (B) SS-02, SS-05, SS-29, SS-30, SS-31, SS-32 and Dmt reduced rate of LDL oxidation.
Figure 3A:
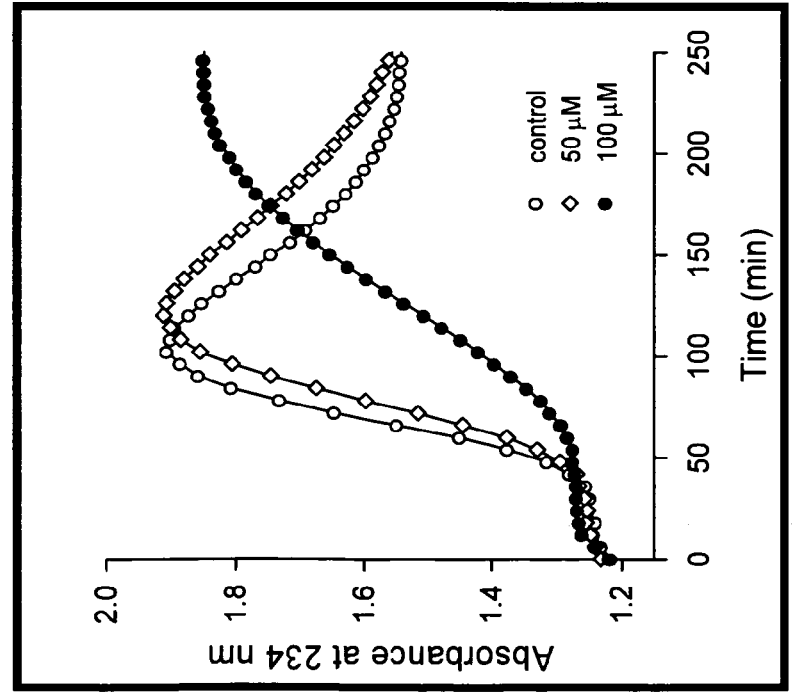

Inhibition of LDL Oxidation (FIG. 3)

Human LDL (low density lipoprotein) was prepared fresh from stored plasma. LDL oxidation was induced catalytically by the addition of 10 mM $CuSO_4$, and the formation of conjugated dienes was monitored at 234 nm for 5 h at 37° C. (B. Moosmann and C. Behl, *Mol Pharmacol* 61, 260-268 (2002)).

(A) Results show that SS-02 dose-dependently inhibited the rate of LDL oxidation.

(B) Various peptides were added in concentration of 100 µM. With the exception of SS-20 (Phe-D-Arg-Phe-Lys-$NH_2$), SS-21 (Cyclohexyl-D-Arg-Phe-Lys-$NH_2$) and SS-22 (Ala-D-Arg-Phe-Lys-$NH_2$), all other SS peptides reduced the rate of linoleic acid peroxidation (reduced rate of formation of conjugated dienes). Note that SS-20, SS-21 and SS-22 do not contain either tyrosine or dimethyltyrosine residues. SS-29 is Dmt-D-Cit-Phe Lys-$NH_2$, SS-30 is Phe-D-Arg-Dmt-Lys-$NH_2$, SS-32 is Dmt-D-Arg-Phe-Ahp(2-aminoheptanoic acid)-$NH_2$.

Example 6

Hydrogen Peroxide Production by Isolated Mouse Liver Mitochondria (FIG. 4)

Because mitochondria are a major source of ROS production, the effect of SS-02 on $H_2O_2$ formation in isolated mitochondria under basal conditions as well as after treatment with antimycin, a complex III inhibitor was examined. Livers were harvested from mice and homogenized in ice-cold buffer and centrifuged at 13800×g for 10 min. The pellet was washed once and then re-suspended in 0.3 ml of wash buffer and placed on ice until use. $H_2O_2$ was measured using luminol chemiluminescence as described previously (Y. Li, H. Zhu, M. A. Trush, *Biochim. Biophys. Acta* 1428, 1-12 (1999)). 0.1 mg mitochondrial protein was added to 0.5 ml potassium phosphate buffer (100 mM, pH 8.0) in the absence or presence of SS peptides (100 µM). 25 mM luminol and 0.7 IU horseradish peroxidase were added, and chemilumunescence was monitored with a Chronolog Model 560 aggregometer (Havertown, Pa.) for 20 min at 37° C. The amount of $H_2O_2$ produced was quantified as the area under the curve (AUC) over 20 min and all data were normalized to AUC produced by mitochondria alone.

(A) The amount of $H_2O_2$ production was significantly reduced in the presence of 10 µM SS-02. Addition of antimycin (1 µM) significantly increased $H_2O_2$ production by isolated mitochondria, and the increase was completely blocked by 10 µM $Dmt^1$-DALDA (also referred to as dDALDA in the specification).

(B) The amount of $H_2O_2$ generated was significantly reduced by peptides SS-02, SS-29, SS-30 and SS-31. SS-21 and SS-22 had no effect on $H_2O_2$ production. Note that SS-21 and SS-22 do not contain a tyrosine or dimethyltyrosine residue. The amino acid Dmt (dimethyltyrosine) alone also inhibited $H_2O_2$ generated.

Example 7

SS-31 Inhibits $H_2O_2$ Generation by Isolated Mitochondria (FIG. 5)

$H_2O_2$ was measured using luminol chemiluminescence as described previously (Y. Li, H. Zhu, M. A. Trush, *Biochim. Biophys. Acta* 1428, 1-12 (1999)). 0.1 mg mitochondrial protein was added to 0.5 ml potassium phosphate buffer (100 mM, pH 8.0) in the absence or presence of SS-31. 25 mM luminol and 0.7 IU horseradish peroxidase were added, and chemilumunescence was monitored with a Chronolog Model 560 aggregometer (Havertown, Pa.) for 20 min at 37° C. The amount of $H_2O_2$ produced was quantified as the area under the curve (AUC) over 20 min, and all data were normaliized to AUC produced by mitochondria alone.

(A) SS-31 dose-dependently reduced the spontaneous production of $H_2O_2$ by isolated mitochondria.

(B) SS-31 dose-dependently reduced the production of $H_2O_2$ induced by antimycin in isolated mitochondria.

Example 8

Figure 6A:
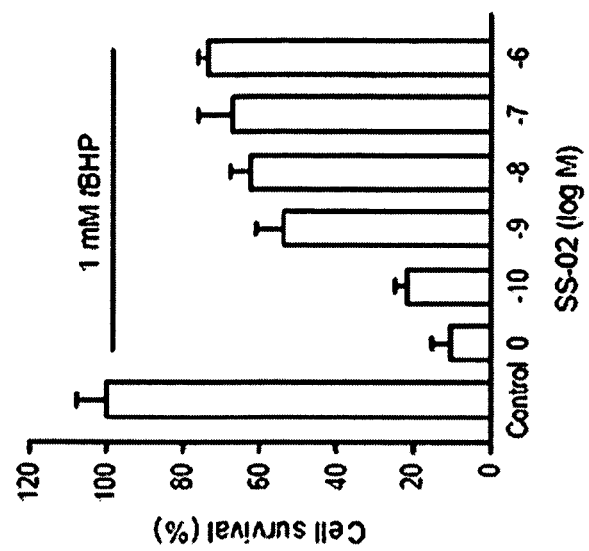
FIG. 6. SS-31 dose-dependently decreased intracellular ROS (reactive oxygen species) (A) and increased cell survival (B) in $N_2A$ cells exposed to a high dose of the pro-oxidant t-butyl hydroperoxide (t-BHP; 0.5 mM), (C) SS-02 also dose-dependently increased cell survival when N2A cells were exposed to 1 mM t-BHP.
Figure 6B:
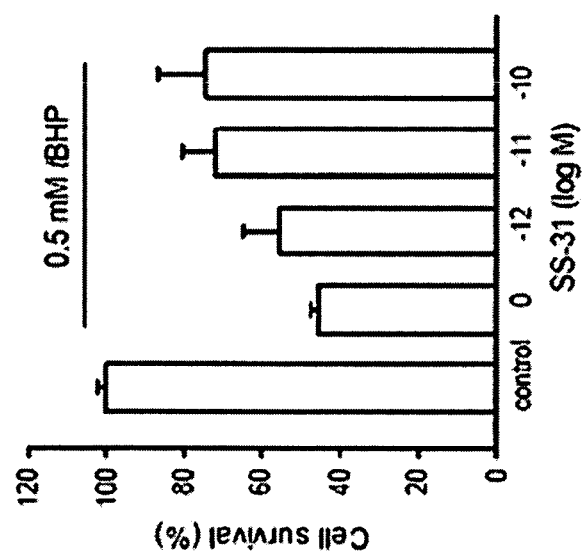
Figure 6C:
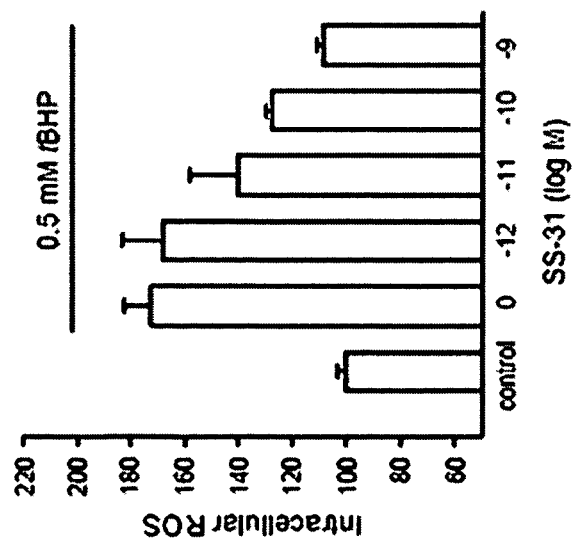

SS-02 and SS-31 Reduced Intracellular ROS and Increased Cell Survival (FIG. 6)

To show that the claimed peptides are effective when applied to whole cells, neuronal $N_2A$ cells were plated in 96-well plates at a density of $1 \times 10^4$/well and allowed to grow for 2 days before treatment with tBHP (0.5 or 1 mM) for 40 min. Cells were washed twice and replaced with medium alone or medium containing varying concerntrations of SS-02 or SS-31 for 4 hr. Intracellular ROS was measured by carboxy-H2DCFDA (Molecular Probes, Portland, Oreg.). Cell death was assessed by a cell proliferation assay (MTS assay, Promega, Madison, Wis.).

Incubation with tBHP resulted in dose-dependent increase in intracellular ROS (A) and decrease in cell viability (B and C). Incubation of these cells with either SS-31 or SS-02 dose-dependently reduced intracellular ROS (A) and increased cell survival (B and C), with EC50 in the nM range.

Example 9

Figure 7A:
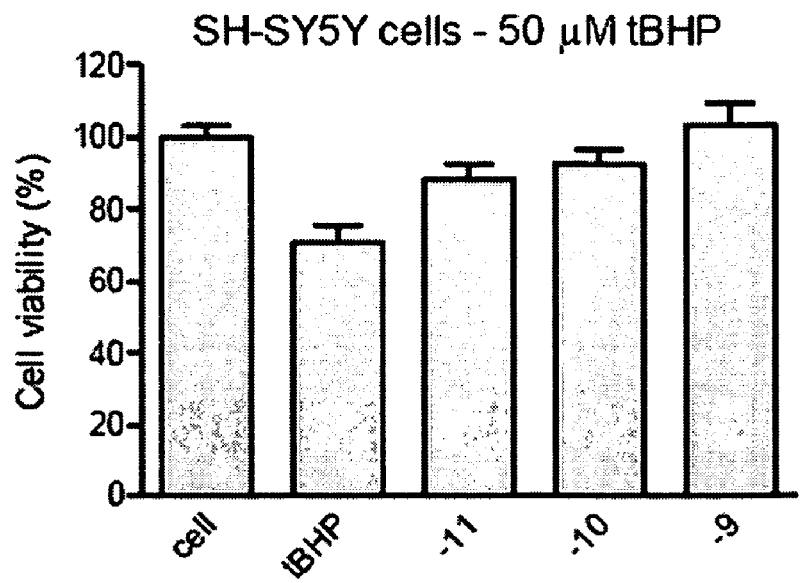
FIG. 7. SS-31 dose-dependently prevented loss of cell viability caused by low doses of t-BHP (0.05-0.1 mM) in neuronal (A) SH-SY5Y and (B) $N_2A$ cells.
Figure 7B:
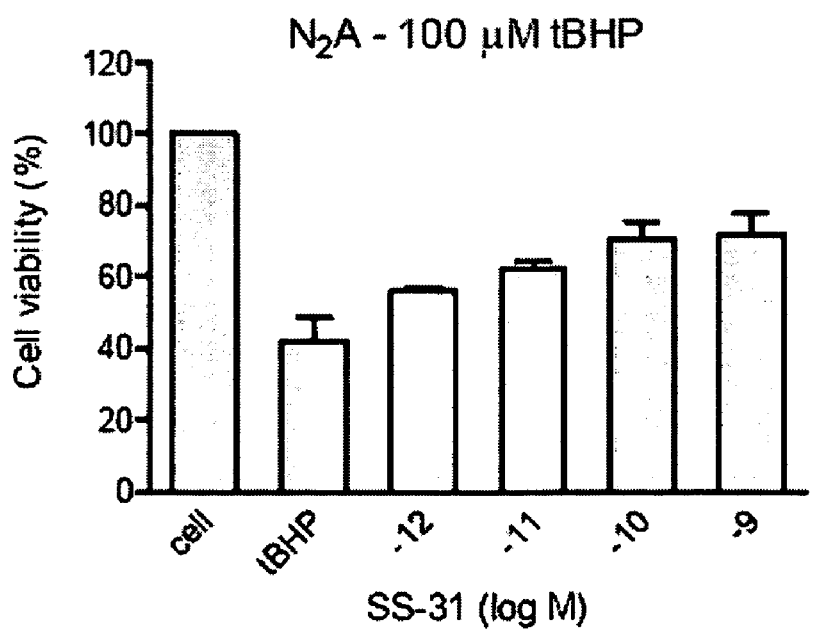

SS-31 Prevented Loss of Cell Viability (FIG. 7)

Neuronal $N_2A$ and SH-SY5Y cells were plated in 96-well plate at a density of $1 \times 10^4$/well and allowed to grow for 2 days before treatment with t-butyl hydroperoxide (tBHP) (0.05-0.1 mM) with or without SS-31 ($10^{-12}$ M to $10^{-9}$ M for 24 h. Cell death was assessed by a cell proliferation assay (MTS assay, Promega, Madison, Wis.).

Treatment of $N_2A$ and SH-SY5Y cells with low doses of t-BHP (0.05-0.1 mM) for 24 h resulted in a decrease in cell viability. (A) 0.05 mM t-BHP induced 50% loss of cell viability in $N_2A$ cells and 30% in SH-SY5Y cells. (B) 0.1 mM t-BHP resulted in a greater reduction in cell viability in SH-SY5Y cells. Concurrent treatment of cells with SS-31 resulted in a dose-dependent reduction of t-BHP-induced cytotoxicity. Complete protection against t-BHP was achieved by 1 nM SS-31.

Example 10

Figure 8:
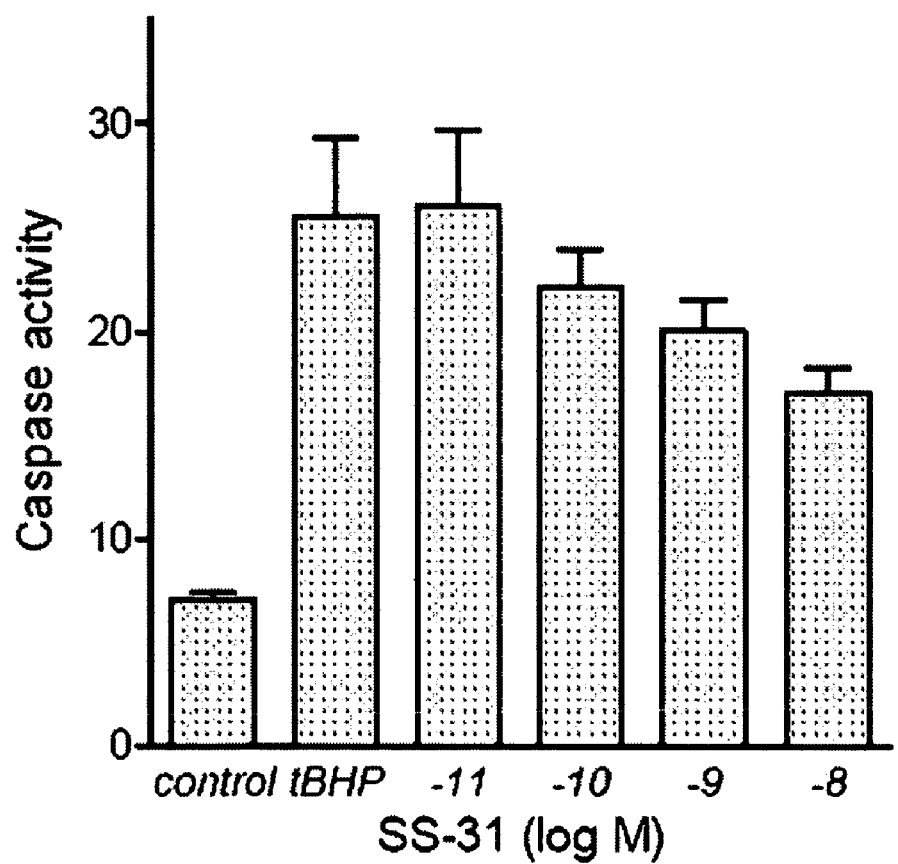
FIG. 8. SS-31 dose-dependently decreased the percent of cells showing increased caspase activity after treatment with a low dose of t-BHP for 12 h in $N_2A$ cells.

SS-31 Decreased Caspase Activity (FIG. 8)

$N_2A$ cells were grown on 96-well plates, treated with t-BHP (0.05 mM) in the absence or presence of SS-31 ($10^{-11}$ M-$10^{-8}$ M) at 37° C. for 12-24 h. All treatments were carried out in quadriplicates. $N_2A$ cells were incubated with t-BHP (50 mM) with or without SS-31 at 37° C. for 12 h. Cells were gently lifted from the plates with a cell detachment solution (Accutase, Innovative Cell Technologies, Inc., San Diego, Calif.) and washed twice in PBS. Caspase activity was assayed using the FLICA kit (Immunochemistry Technologies LLC, Bloomington, Minn.). According to the manufacturer's recommendation, cells were resuspended (approx. $5 \times 10^6$ cells/ml) in PBS and labeled with pan-caspase inhibitor FAM-VAD-FMK for 1 h at 37° C. under 5% $CO_2$ and protected from the light. Cells were then rinsed to remove the unbound reagent and fixed. Fluorescence intensity in the cells was measured by a laser scanning cytometer (Beckman-Coulter XL, Beckman Coulter, Inc., Fullerton, Calif.) using the standard emission filters for green (FL1). For each run, 10,000 individual events were collected and stored in list-mode files for off-line analysis.

Caspase activation is the initiating trigger of the apoptotic cascade, and our results showed a significant increase in caspase activity after incubation of SH-SY5Y cells with 50 mM t-BHP for 12 h which was dose-dependently inhibited by increasing concentrations of SS-31.

Example 11

Figure 9:
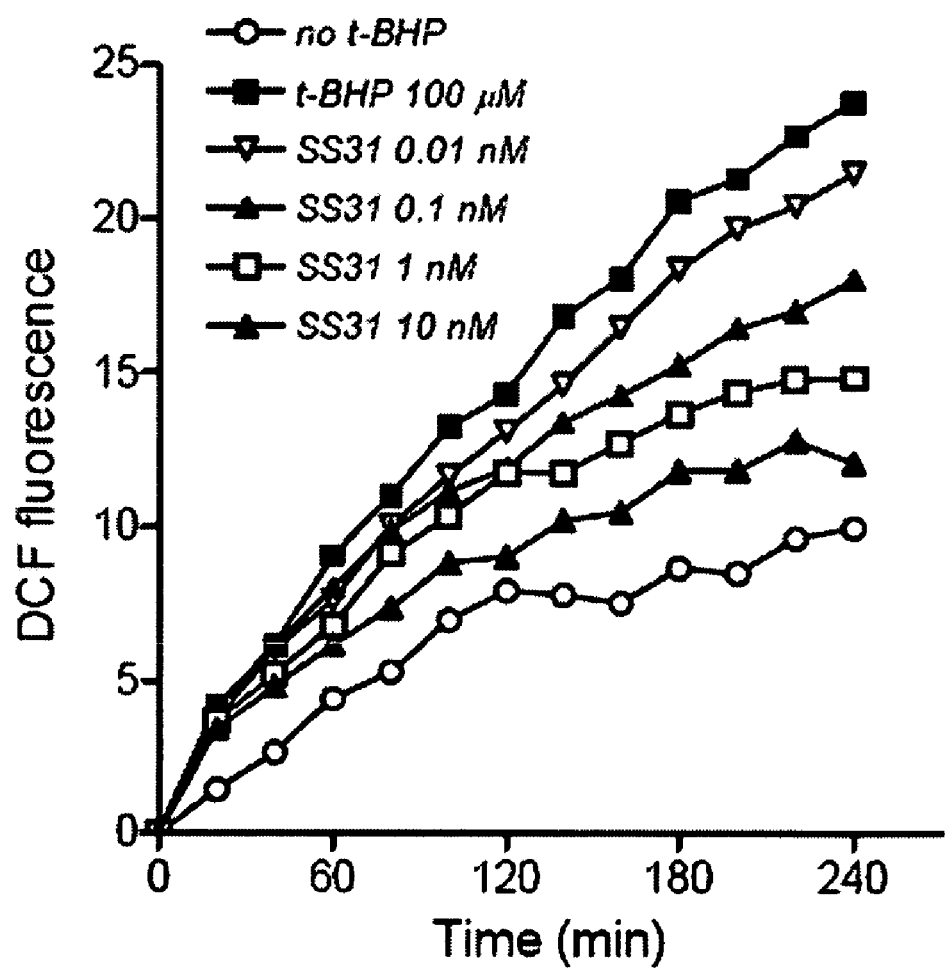
FIG. 9. SS-31 dose-dependently reduced the rate of ROS accumulation in $N_2A$ cells with 0.1 mM t-BHP over a 4 h period.

SS-31 Reduced Rate of ROS Accumulation (FIG. 9)

Intracellular ROS was evaluated using the fluorescent probe DCFH-DA (5-(and -6)-carboxy-2',7'-dichlorodihydrofluorescein diacetate). DCFH-DA enters cells passively and is then deacetylated to nonfluorescent DCFH. DCFH reacts with ROS to form DCF, the fluorescent product. $N_2A$ cells in 96 sell plates were washed with HBSS and loaded with 10 µM of DCFDA for 30 min. for 30 min. at 37° C. Cells were washed 3 times with HBSS and exposed to 0.1 mM of t-BHP, alone or with SS-31. The oxidation of DCFH to DCF was monitored in real time by a fluorescence microplate reader (Molecular Devices) using 485 nm for excitation and 530 nm for emission.

The rate of ROS accumulation in $N_2A$ cells treated with 0.1 mM t-BHP was dose-dependently inhibited by the addition of SS-31.

Example 12

Figure 10:
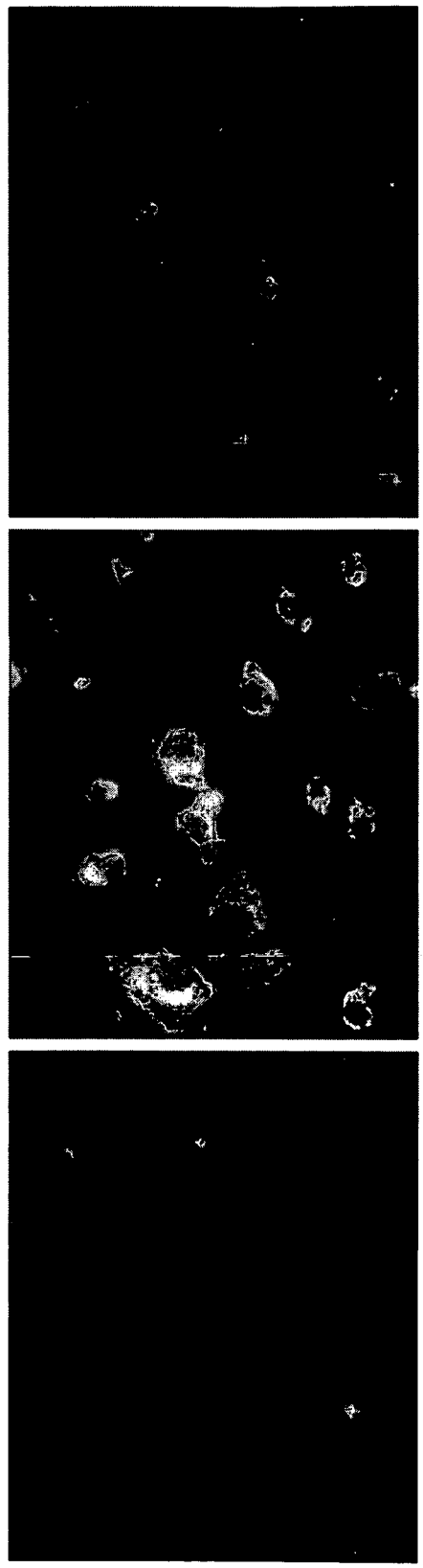
FIG. 10. SS-31 inhibited lipid peroxidation caused by exposure of $N_2A$ cells to 1 mM t-BHP for 1 h. (A) untreated cells; (B) cells treated with 1 mM t-BHP for 3 h; (C) cells treated with 1 mM t-BHP and 10 nM SS-31 for 3 h.

SS-31 Inhibited Lipid Peroxidation in Cells Exposed to Oxidative Damage (FIG. 10)

SS-31 inhibited lipid peroxidation in $N_2A$ cells treated with t-BHP. Lipid peroxidation was evaluated by measuring HNE Michael adducts. 4-HNE is one of the major aldehydic products of the peroxidation of membrane polyunsaturated fatty acids. $N_2A$ cells were seeded on glass bottom dish 1 day before t-BHP treatment (1 mM, 3 h, 37° C., 5% $CO_2$) in the presence of absence of SS-31 ($10^{-8}$ to $10^{-10}$ M). Cells were then washed twice with PBS and fixed 30 min with 4% paraformaldehyde in PBS at RT and then washed 3 times with PBS. Cells were then permeabilized, treated with rabbit anti-HNE antibody followed by the secondary antibody (goat anti-rabbit IgG conjugated to biotin). Cells were mounted in Vectashield and imaged using a Zeiss fluorescence microscope using an excitation wavelength of 460±20 nm and a longpass filter of 505 nm for emission.

(A) Untreated cells; (B) cells treated with 1 mM t-BHP for 3 h; (C) cells treated with 1 mM t-BHP and 10 nM SS-31 for 3 h.

Example 13

SS-02 Inhibits Loss of Mitochondrial Potential in Cells Exposed to hydrogen Peroxide Caco-2 cells were treated with tBHP (1 mM) in the absence or presence of SS-02 (0.1 µM) for 4 h, and then incubated with TMRM and examined under LSCM. In control cells, the mitochondria are clearly visualized as fine streaks throughout the cytoplasm. In cells treated with tBHP, the TMRM fluorescence is much reduced, suggesting generalized depolarization. In contrast, concurrent treatment with SS-02 protected against mitochondrial depolarization caused by tBHP.

Example 14

Figure 11:
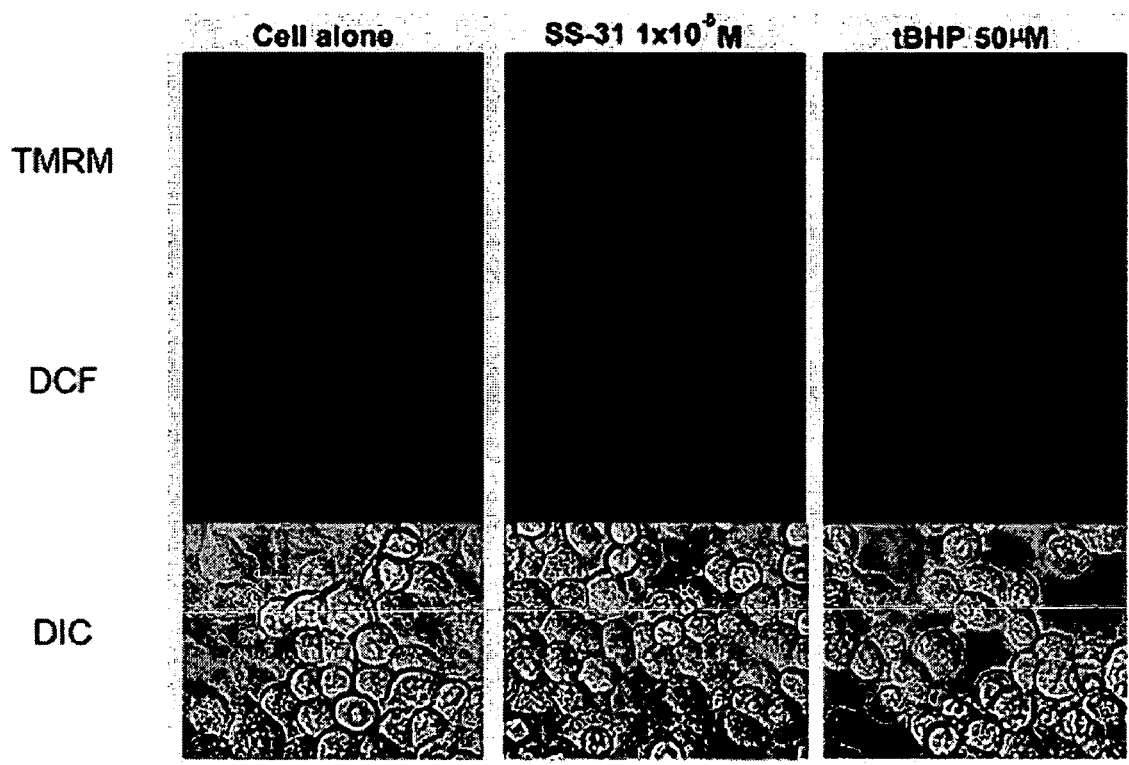
FIG. 11. SS-31 prevented mitochondrial depolarization and ROS accumulation in $N_2A$ cells exposed to t-BHP.

SS-31 Prevents Loss of Mitochondrial Potential and Increased ROS Accumulation in $N_2A$ Cells Caused by Exposure to t-BHP (FIG. 11)

$N_2A$ cells in glass bottom dish were treated with 0.1 mM t-BHP, alone or with 1 nM SS-31, for 6 h. Cells were then loaded with 10 µm of dichlorofluorescin (ex/em=485/530) for 30 min at 37° C., 5% $CO_2$. Then cells were subjected 3 times wash with HBSS and stained with 20 nM of Mitotracker TMRM (ex/em=550/575 nm) for 15 min at 37° C., and examined by confocal laser scanning microscopy.

Treatment of $N_2A$ cells with t-BHP resulted in loss of TMRM fluorescence indicating mitochondrial depolarization. There was also a concomitant increase in DCF fluorescence indicating increase in intracellular ROS. Concurrent treatment with 1 nM SS-31 prevented mitochondrial depolarization and reduced ROS accumulation.

Example 15

Figure 12D:
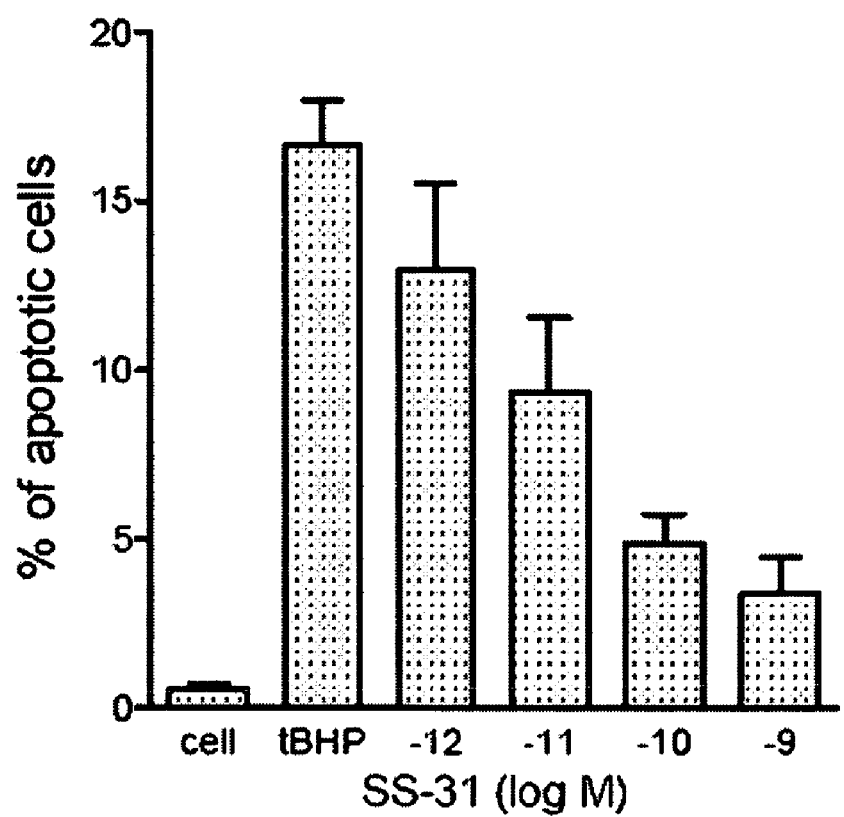
FIG. 12. SS-31 prevents apoptosis induced by a low dose of t-BHP. Apoptosis was evaluated by confocal microscopy with the fluorescent probe Hoechst 33342. (A1) a representative field of cells not treated with t-BHP. (A2) Fluorescent image showing a few cells with dense, fragmented chromatin indicative of apoptotic nuclei. (B1) A representative field of cells treated with 0.025 mM t-BHP for 24 h. (B2) Fluorescent image showing an increased number of cells with apoptotic nuclei. (C1) A representative field of cells treated with 0.025 mM t-BHP and 1 nM SS-31 for 24 h. (C2) Fluorescent image showing a reduced number of cells with apoptotic nuclei. (D) SS-31 dose-dependently reduced the percent of apoptotic cells caused by 24 h treatment with a low dose of t-BHP (0.05 mM).

SS-31 Prevents Apoptosis Caused by Oxidative Stress (FIG. 12)

SH-SY5Y cells were grown on 96-well plates, treated with t-BHP (0.025 mM) in the absence or presence of SS-31 ($10^{-12}$ M-$10^{-9}$ M) at 37° C. for 24 h. All treatments were carried out in quadriplicates. Cells were then stained with 2 mg/ml Hoechst 33342 for 20 min, fixed with 4% paraformaldehyde, and imaged using a Zeiss fluorescent microscope (Axiovert 200M) equipped with the Zeiss Acroplan x20 objective. Nuclear morphology was evaluated using an excitation wavelength of 350±10 nm and a longpass filter of 400 nm for emission. All images were processed and analyzed using the MetaMorph software (Universal Imaging Corp., West Chester, Pa.). Uniformly stained nuclei were scored as healthy, viable neurons, while condensed or fragmented nuclei were scored as apoptotic.

SS-31 prevents apoptosis induced by a low dose of t-BHP. Apoptosis was evaluated by confocal microscopy with the fluorescent probe Hoechst 33342. (A1) a representative field of cells not treated with t-BHP. (A2) Fluorescent image showing a few cells with dense, fragmented chromatin indicative of apoptotic nuclei. (A3) A representative field of cells treated with 0.025 mM t-BHP for 24 h. (A4) Fluorescent image showing an increased number of cells with apoptotic nuclei. (A5) A representative field of cells treated with 0.025 mM t-BHP and 1 nM SS-31 for 24 h. (A6) Fluorescent image showing a reduced number of cells with apoptotic nuclei.

(B) SS-31 dose-dependently reduced the percent of apoptotic cells caused by 24 h treatment with a low dose of t-BHP (0.05 mM).

Example 16

Figure 13A:
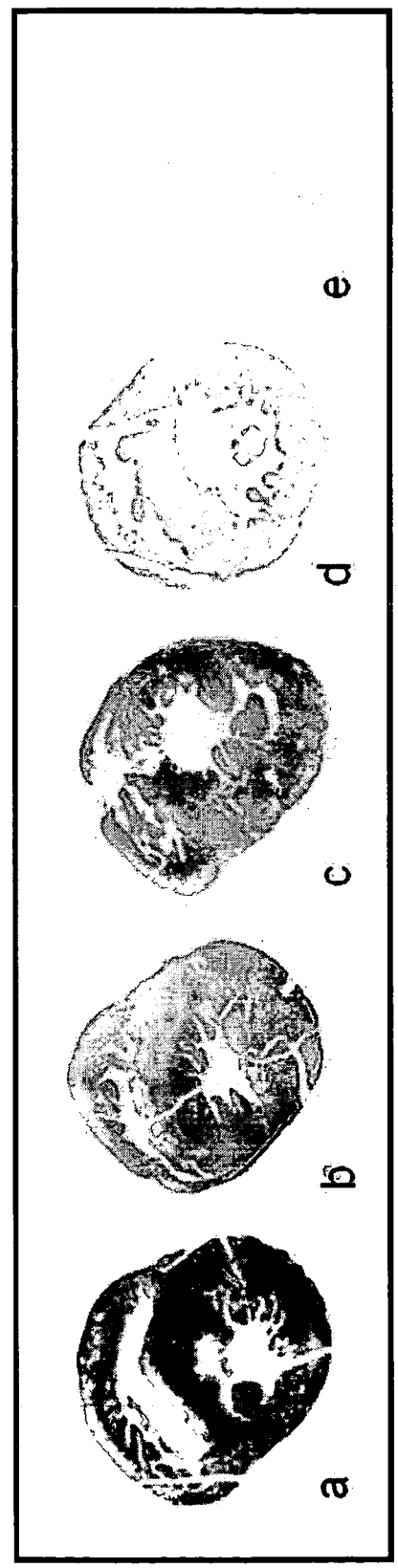
FIG. 13A. SS-02 and SS-31 reduced lipid peroxidation in isolated guinea pig hearts subjected to warm reperfusion after a brief period of ischemia. Immunohistochemical analysis of 4-hydroxy-2-nonenol (HNE)-modified proteins in paraffin sections from guinea pig hearts aerobically perfused 30 min with (a) buffer; (b) 100 nM SS-02; (c) 100 nM SS-20 and (d) 1 nM SS-31, then subjected to 30 min ischemia and reperfused for 90 min with corresponding peptides. Tissue slices were incubated with anti-HNE antibody. (e) Background control: staining without primary antibody.
Figure 13B:
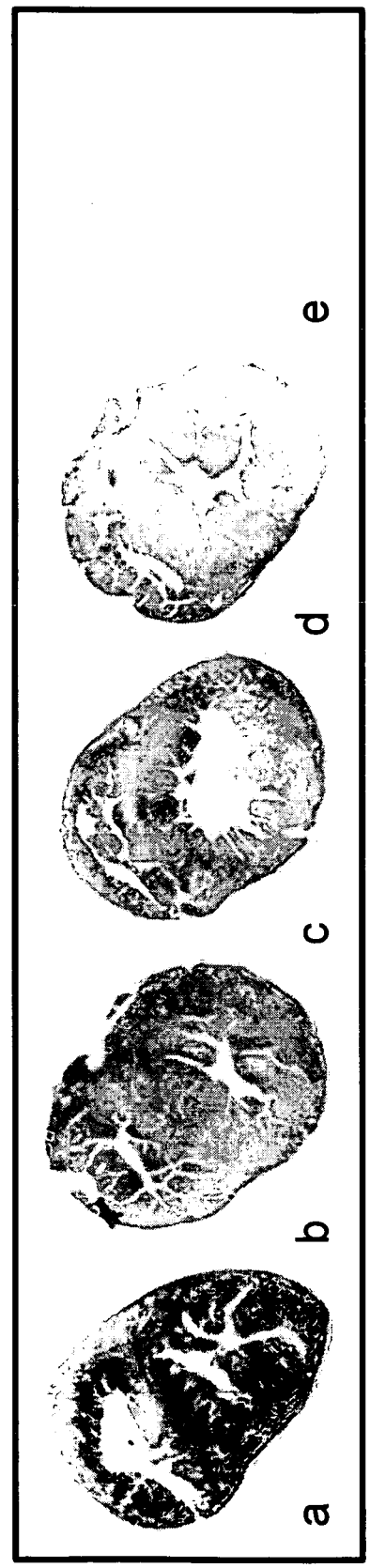
FIG. 13B. SS-02 and SS-31 reduced lipid peroxidation in isolated guinea pig hearts subjected to warm reperfusion after a brief period of ischemia. Immunohistochemical analysis of 4-hydroxynonenol (HNE)-modified proteins in paraffin sections from guinea pig hearts aerobically perfused 30 min with buffer; then subjected to 30 min ischemia and reperfused with (a) buffer; (b) 100 nM SS-02; (c) 100 nM SS-20 and (d) 1 nM SS-31 for 90 min. Tissue slices were incubated with anti-HNE antibody. (e) Background control: staining without primary antibody.

SS-31 Prevents Lipid Peroxidation in Hearts Subjected to Brief Intervals of Ischemia-Reperfusion (FIG. 13)

Isolated guinea pig hearts were perfused in a retrograde manner in a Langendorff apparatus and subjected to various intervals of ischemia-reperfusion. Hearts were then fixed immediately and embedded in paraffin. Immunohistochemical analysis of 4-hydroxy-2-nonenol (HNE)-modified proteins in the paraffin sections was carried out using an anti-HNE antibody.

(A) Immunohistochemical analysis of 4-hydroxy-2-nonenol (HNE)-modified proteins in paraffin sections from guinea pig hearts aerobically perfused 30 min with (a) buffer; (b) 100 nM SS-02; (c) 100 nM SS-20 and (d) 1 nM SS-31, then subjected to 30 min ischemia and reperfused for 90 min with same peptides. Tissue slices were incubated with anti-HNE antibody. (e) Background control: staining without primary antibody.

(B) Immunohistochemical analysis of HNE-modified proteins in paraffin sections from guinea pig hearts aerobically perfused 30 min with buffer; then subjected to 30 min ischemia and reperfused with (a) buffer; (b) 100 nM SS-02; (c) 100 nM SS-20 and (d) 1 nM SS-31 for 90 min with same peptides. Tissue slices were incubated with anti-HNE antibody. (e) Background control: staining without primary antibody.

Example 17

Figure 14A:
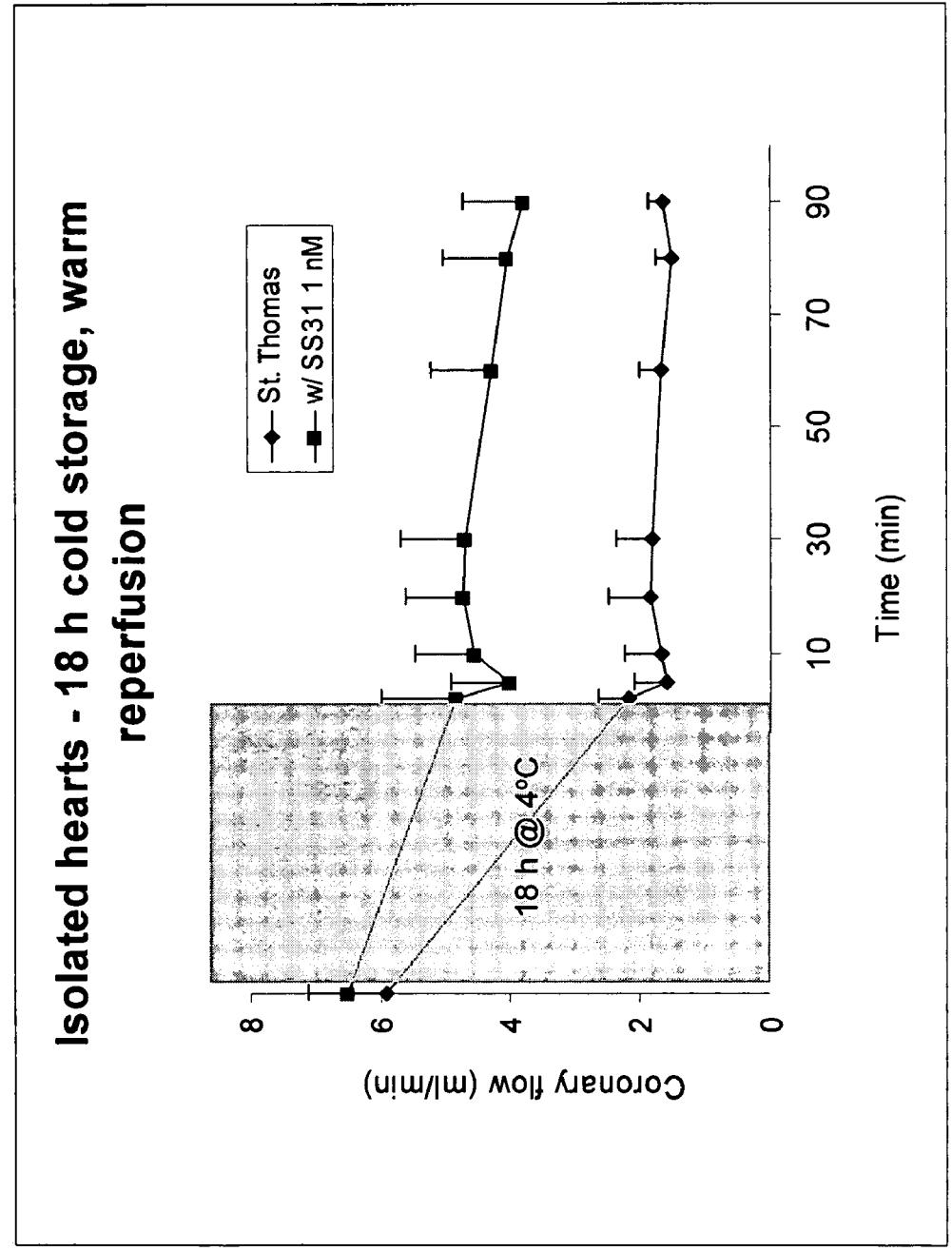
FIG. 14A. SS-31 significantly improved coronary flow in isolated guinea pig hearts subjected to warm reperfusion after prolonged (18 h) cold ischemia. The shaded area represents 18 h of ischemia at 4° C.
Figure 14B:
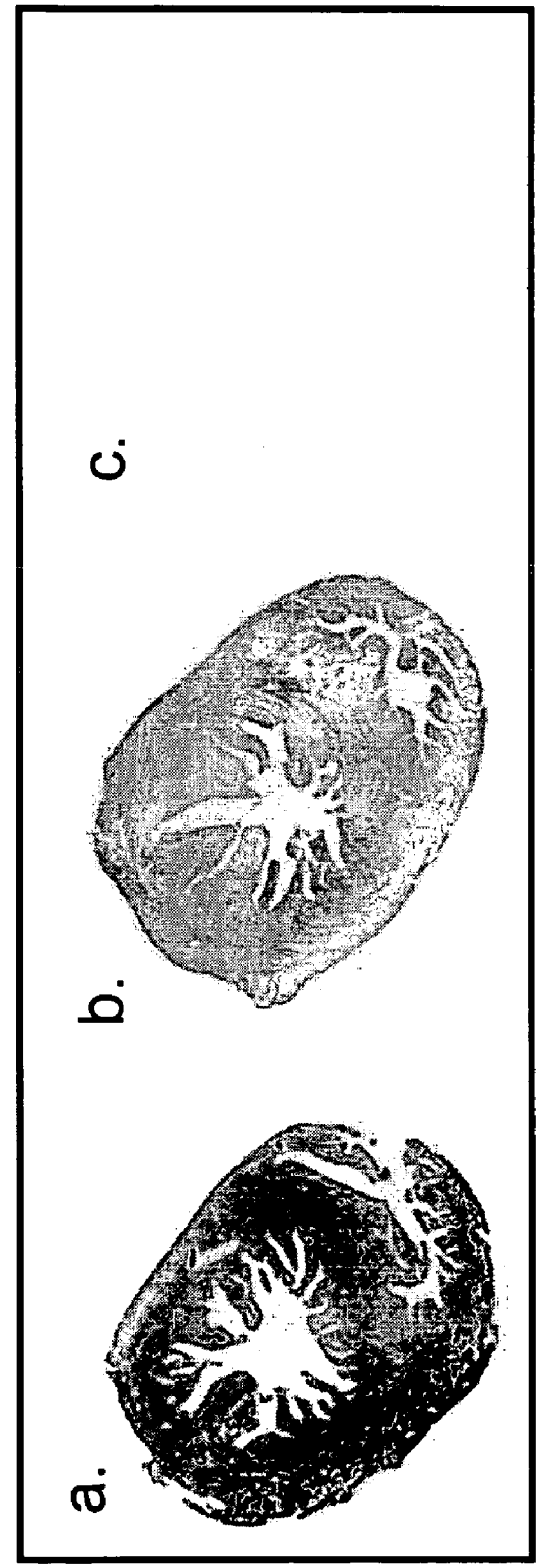
FIG. 14B. Guinea pig hearts perfused with a cardioplegic solution (St. Thomas solution) without (a) or with (b) 1 nM SS-31 for 3 min and then subjected to 18 h of cold ischemia (4° C.), (c) background staining with primary antibody. The hearts were then reperfused with buffer at 34° C. for 90 min.
Figure 14C:
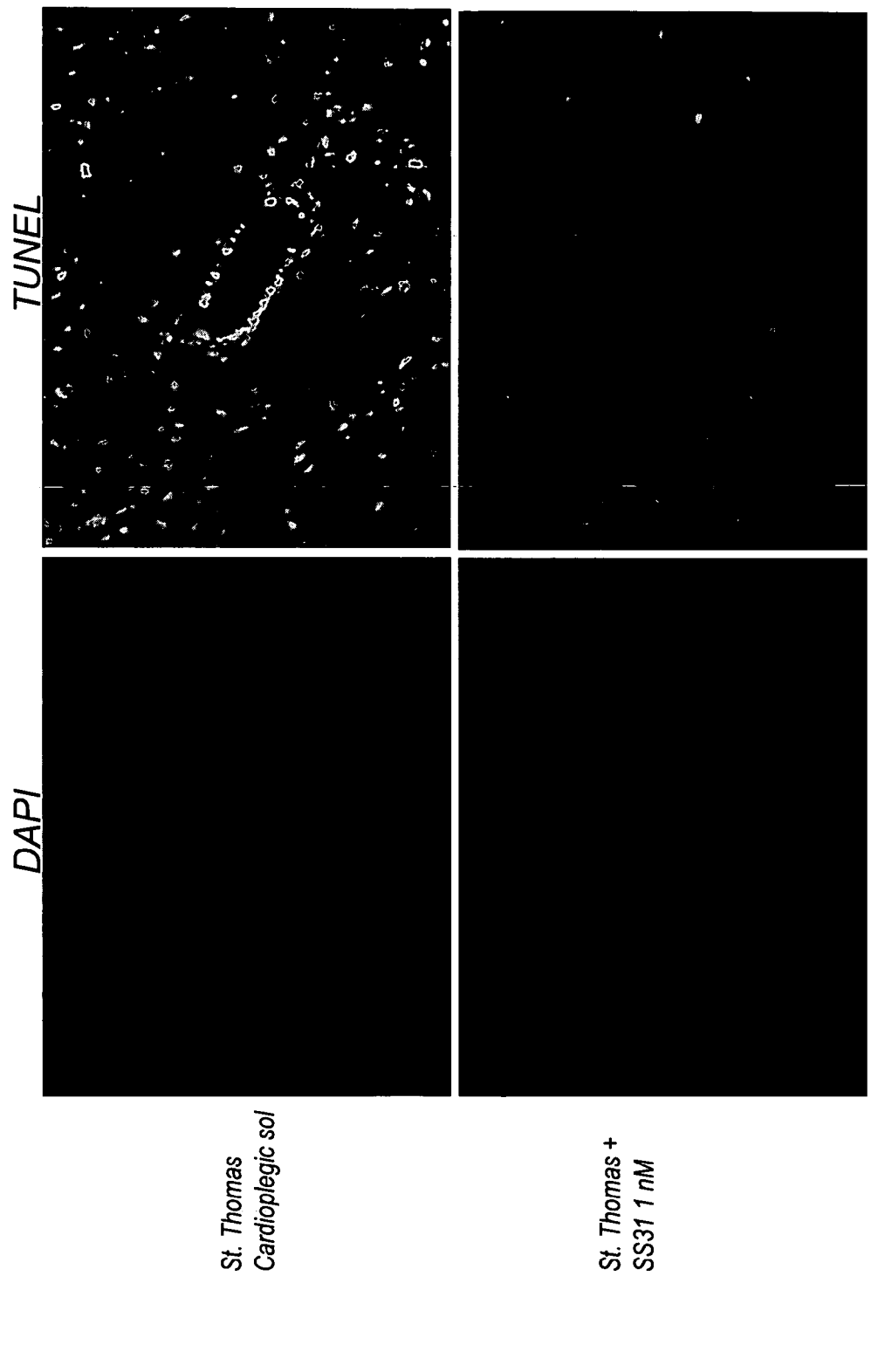
FIG. 14C. SS-31 prevents apoptosis in endothelial cells and myocytes in isolated guinea pig hearts subjected to warm reperfusion after prolonged (18 h) cold ischemia. Guinea pig hearts perfused with a cardioplegic solution (St. Thomas solution) without or with 1 nM SS-31 for 3 min and then subjected to 18 h of cold ischemia (4° C.). The hearts were then reperfused with buffer at 34° C. for 90 min. Apoptosis was assessed by the TUNEL stain (green) and nuclei are visualized by DAPI (blue).

SS-31 Increases Coronary Flow and Reduces Lipid Peroxidation and Apoptosis in Hearts Subjected to Prolonged Cold Ischemia Followed by Warm Reperfusion (FIG. 14)

Isolated guinea pig hearts were perfused in a retrograde manner in a Langendorff apparatus with a cardioplegic solution (St. Thomas solution) without or with SS-31 (1 nM) for 3 min, and then clamped and stored at 4° C. for 18 h. Subsequently the hearts were remounted in the Langendorff apparatus and reperfused with Krebs-Henseleit solution at 34° C. for 90 min. Hearts were then rapidly fixed and paraffin-embedded.

(A) SS-31 significantly improved coronary flow in hearts after 18 h cold ischemic storage. The shaded area represents 18 h of cold ischemia.

(B) Immunohistochemical analysis of HNE-modified proteins in paraffin sections from guinea pig hearts stored without (a) or with (b) SS-31 (1 nM). (c) Background staining without primary antibody.

(C) SS-31 prevents apoptosis in endothelial cells and myocytes in isolated guinea pig hearts subjected to warm reperfusion after prolonged (18 h) cold ischemia. Apoptosis was assessed by the TUNEL stain (green) and nuclei are visualized by DAPI (blue).

Example 18

Figure 15A:
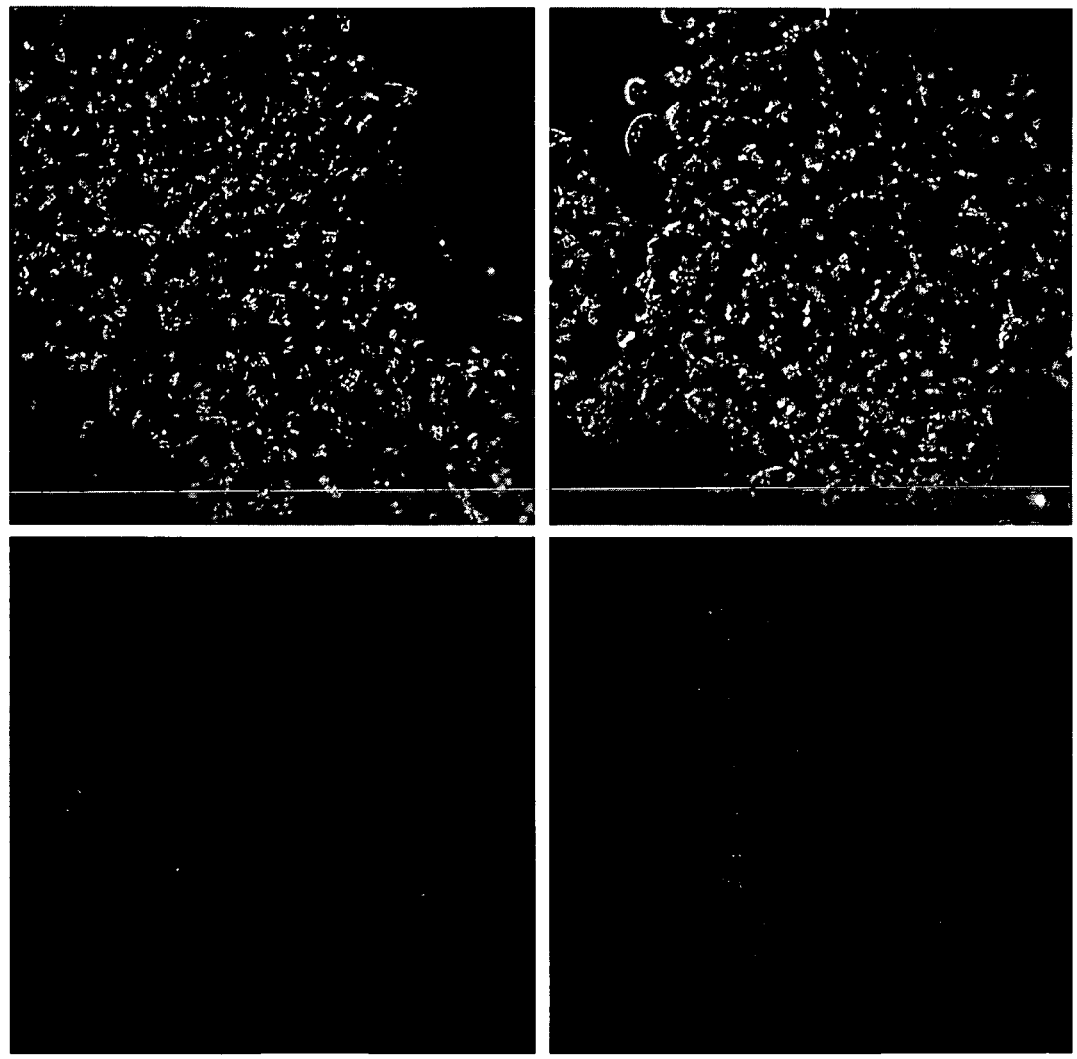
FIG. 15A. SS-31 improves survival of islet cells isolated from mouse pancreas as measured by mitochondrial potential. SS-31 (1 nM) was added to all isolation buffers used throughout the isolation procedure. Mitochondrial potential was measured using TMRM (red) with confocal microscopy.
Figure 15B:
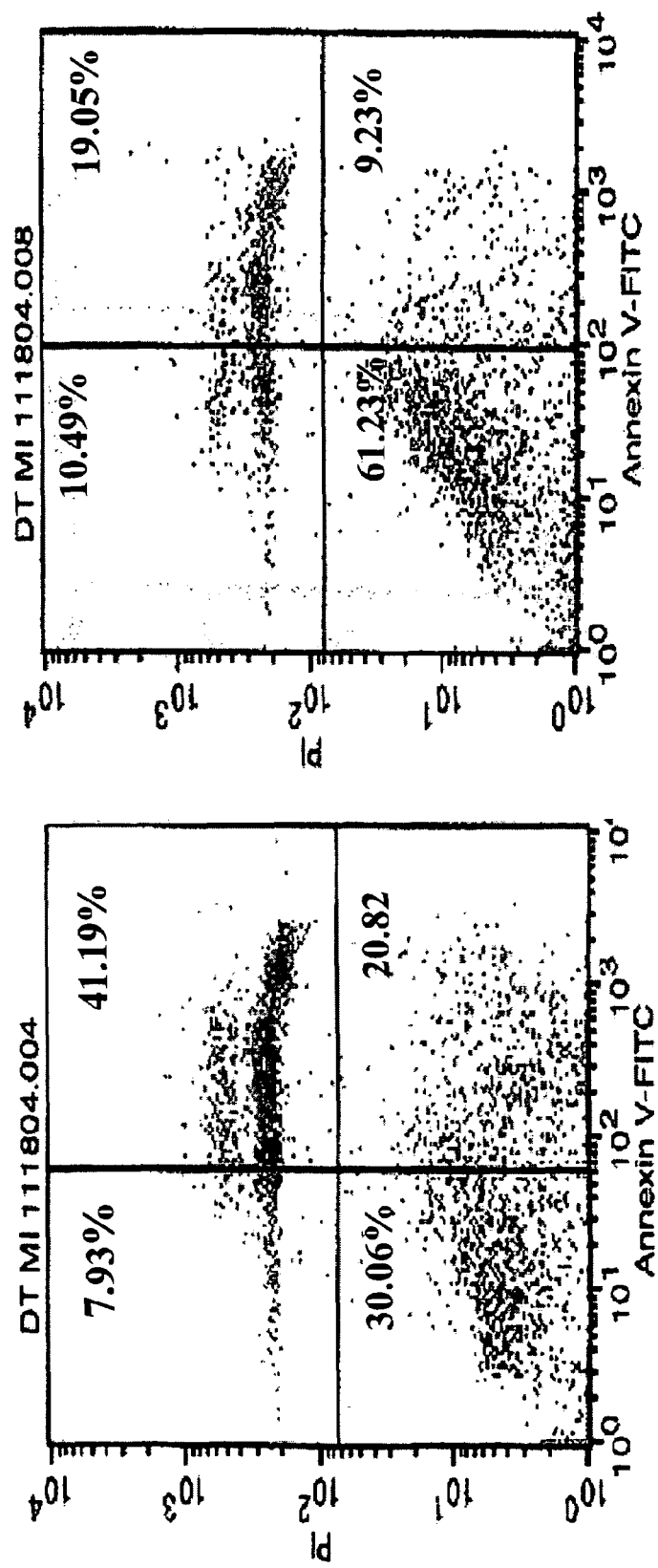
FIG. 15B. SS-31 reduces apoptosis and increases viability in islet cells isolated from mouse pancreas as measured by flow cytometry. SS-31 (1 nM) was added to all isolation buffers used throughout the isolation procedure. Apoptosis was ascertained using annexin V and necrosis by propidium iodide (PI).

SS-31 Improves Survival of Islet Cells Isolated from Mouse Pancreas (FIG. 15)

(A) SS-31 improves mitochondrial potential in islet cells isolated from mouse pancreas. Pancreas was harvested from mice and islet cells were prepared according standard procedures. In some studies, SS-31 (1 nM) was added to all isolation buffers used throughout the isolation procedure. Mitochondrial potential was measured using TMRM (red) and visualized by confocal microscopy.

(B) SS-31 reduces apoptosis and increases viability in islet cells isolated from mouse pancreas. Pancreas was harvested from mice and islet cells were prepared according standard procedures. In some studies, SS-31 (1 nM) was added to all isolation buffers used throughout the isolation procedure. Apoptosis was ascertained by flow cytometry using annexin V and necrosis by propidium iodide.

Example 19

Figure 16:
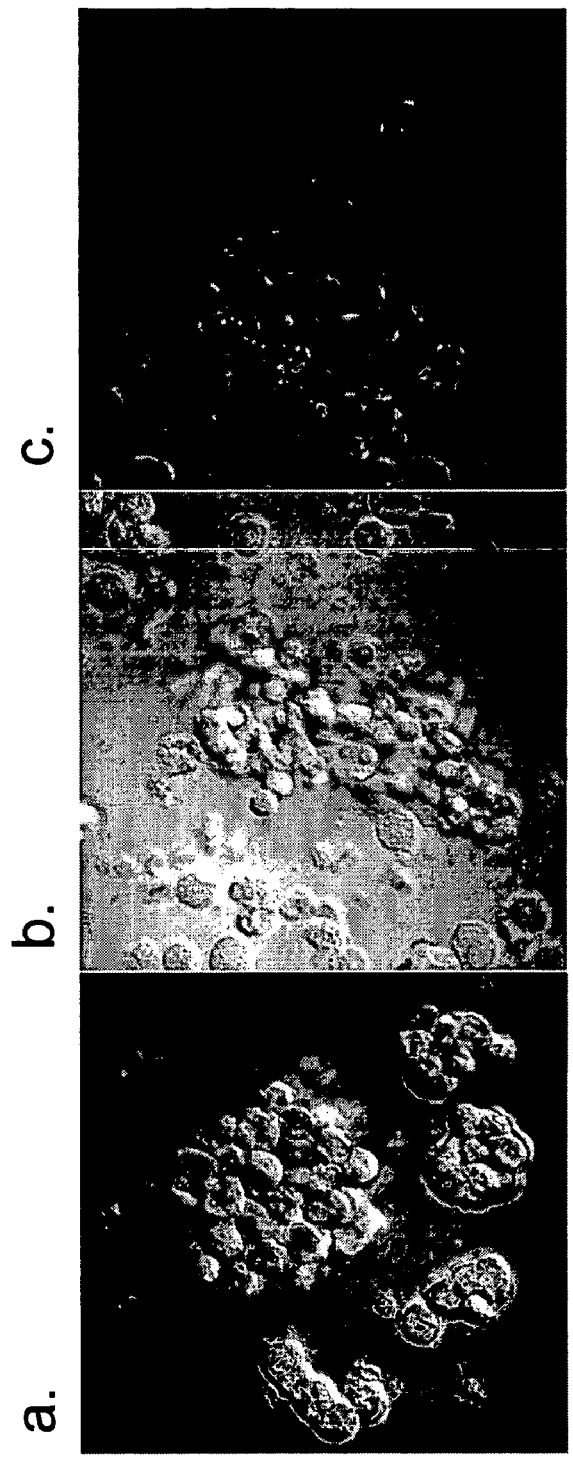
FIG. 16. SS-31 reduces oxidative damage in pancreatic islet cells caused by t-butylhydroperoxide (tBHP). Mouse pancreatic islet cells were untreated (a), or treated with 25 μM tBHP without (b) or with 1 nM SS-31 (c). Mitochondrial potential was measured by TMRM (red) and reactive oxygen species were measured by DCF (green) using confocal microscopy.

SS-31 Protects Against Oxidative Damage in Pancreatic Islet Cells (FIG. 16)

Mouse pancreatic islet cells were untreated (a), or treated with 25 μM tBHP without (b) or with 1 nM SS-31 (c). Mitochondrial potential was measured by TMRM (red) and reactive oxygen species were measured by DCF (green) using confocal microscopy.

Example 20

Figure 17A:
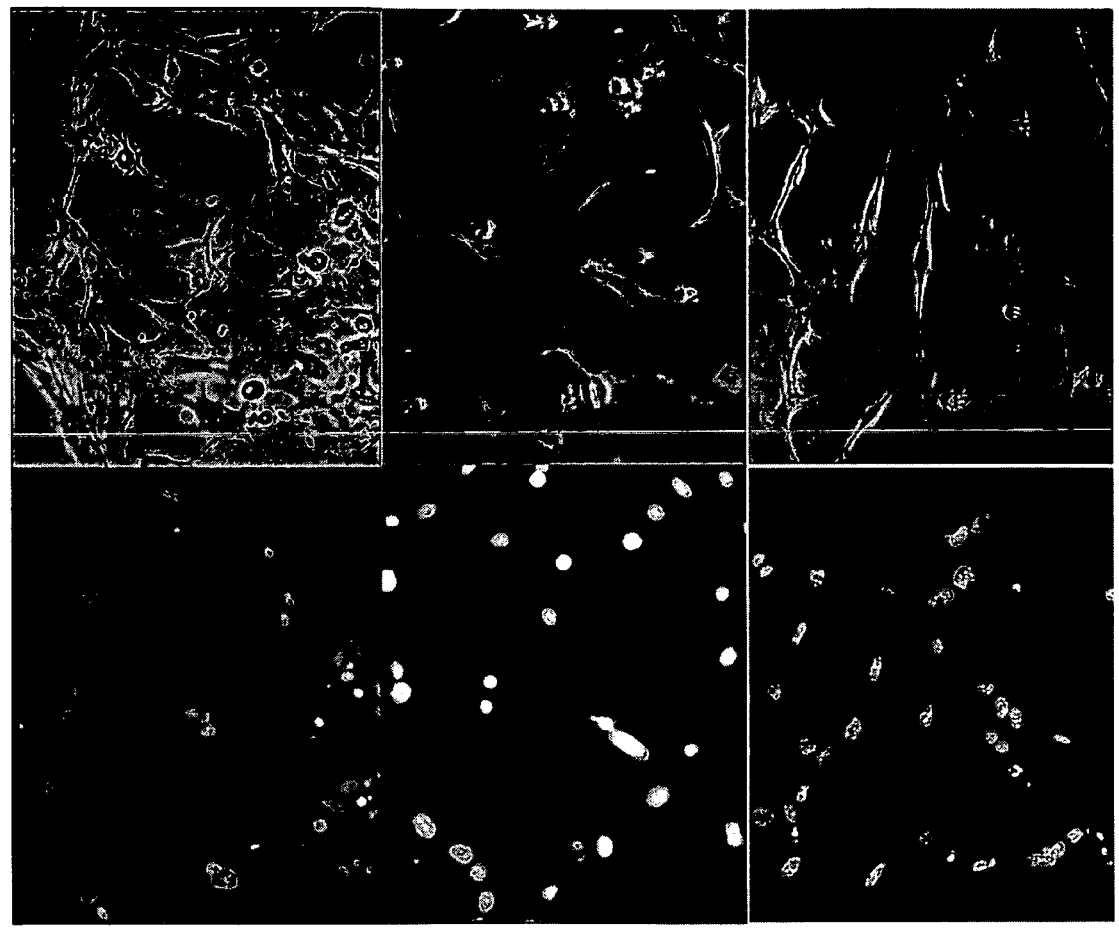
FIG. 17A. SS-31 protects dopamine cells against $MPP^+$ toxicity. SN-4741 cells were treated with buffer, 50 μM $MPP^+$ or 50 μM $MPP^+$ and 1 nM SS-31, for 48 h, and the incidence of apoptosis was determined by fluorescent microscopy with Hoechst 33342. The number of condensed fragmented nuclei was significantly increased by $MPP^+$ treatment. Concurrent treatment with SS-31 reduced the number of apoptotic cells.
Figure 17B:
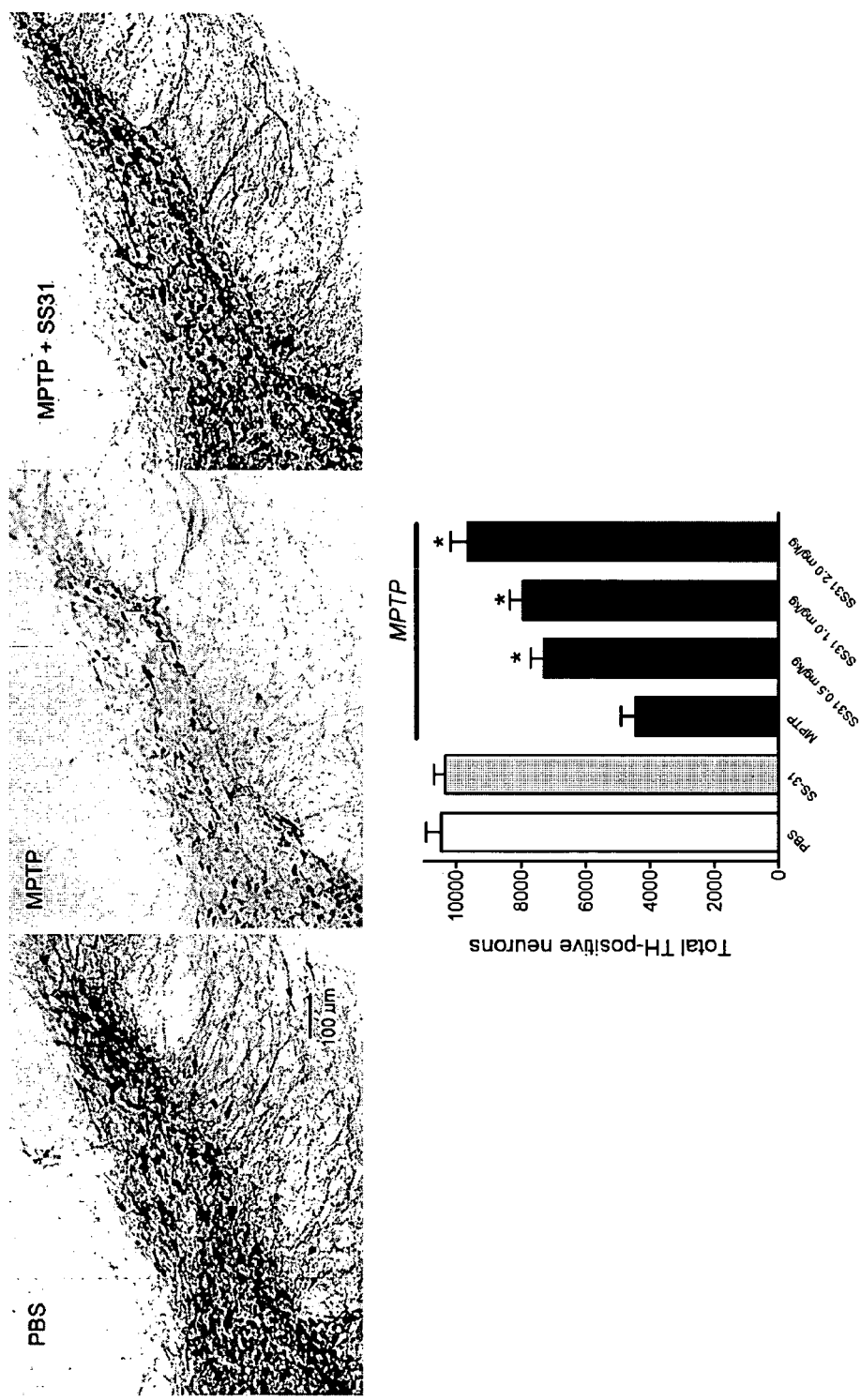
FIG. 17B. SS-31 dose-dependently prevented loss of dopamine neurons in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and striatal brain regions were immunostained for tyrosine hydroxylase activity (shown in black).
Figure 17C:
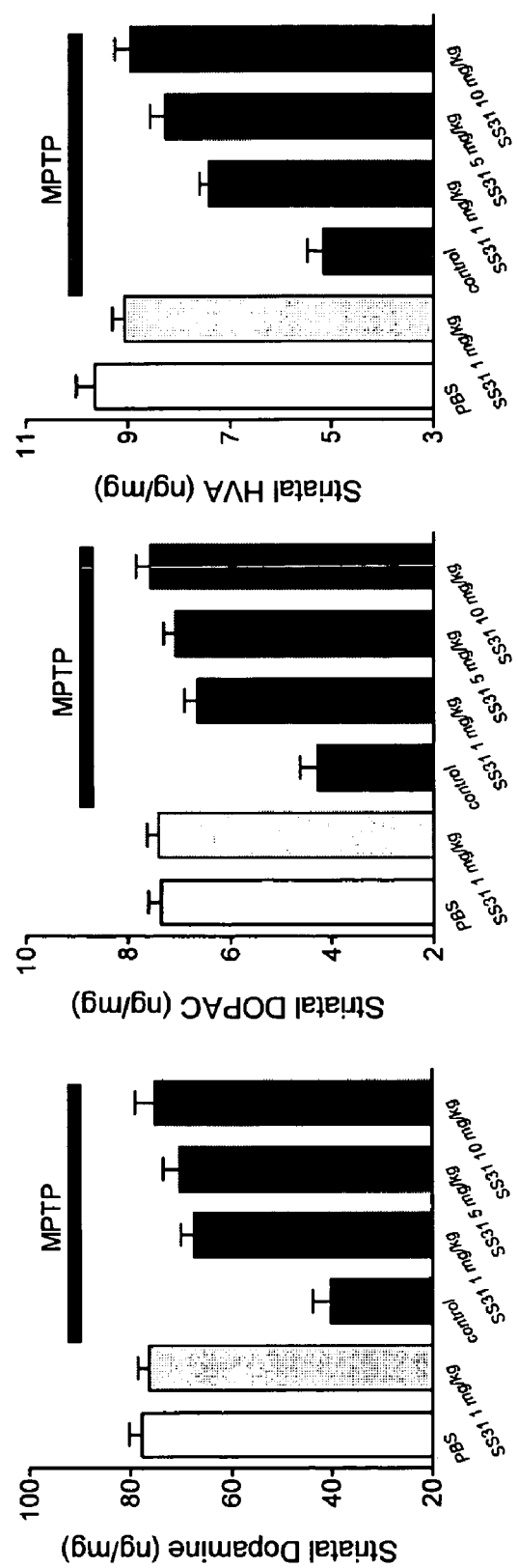
FIG. 17C. SS-31 dose-dependently increased striatal dopamine, DOPAC (3,4-dihydroxyphenylacetic acid) and HVA (homovanillic acid) levels in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and dopamine, DOPAC and HVA levels were quantified by high pressure liquid chromatography.

SS-31 Protects Against Parkinson's Disease (FIG. 17)

MPTP is a neurotoxin that selectively destroys striatal dopamine neurons and can be used as an animal model of Parkinson's Disease. $MPP^+$, a metabolite of MPTP, targets mitochondria, inhibits complex I of the electron transport chain and increases ROS production. $MPP^+$ is used in cell culture studied because cells are unable to metabolize MPTP to the active metabolite. MPTP is used for animal studies.

(A) SS-31 protects dopamine cells against $MPP^+$ toxicity. SN-4741 cells were treated with buffer, 50 μM $MPP^+$ or 50 μM $MPP^+$ and 1 nM SS-31, for 48 h, and the incidence of apoptosis was determined by fluorescent microscopy with Hoechst 33342. The number of condensed fragmented nuclei was significantly increased by $MPP^+$ treatment. Concurrent treatment with SS-31 reduced the number of apoptotic cells.

(B) SS-31 dose-dependently prevented loss of dopamine neurons in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and striatal brain regions were immunostained for tyrosine hydroxylase activity.

(C) SS-31 dose-dependently increased striatal dopamine, DOPAC (3,4-dihydroxyphenylacetic acid) and HVA (homovanillic acid) levels in mice treated with MPTP. Three doses of MPTP (10 mg/kg) was given to mice (n=12) 2 h apart. SS-31 was administered 30 min before each MPTP injection, and at 1 h and 12 h after the last MPTP injection. Animals were sacrificed one week later and dopamine, DOPAC and HVA levels were quantified by high pressure liquid chromatography.

What is claimed is:

1. A method for reducing oxidative damage in a mammal in need thereof, the method comprising administering to the mammal an effective amount of D-Arg-Dmt-Lys-Phe-NH$_2$ peptide.

2. The method according to claim 1, wherein the peptide is administered orally.

3. The method according to claim 1, wherein the peptide is administered topically.

4. The method according to claim 1, wherein the peptide is administered intranasally.

5. The method according to claim 1, wherein the peptide is administered systemically.

6. The method according to claim 3, wherein the peptide is administered intravenously.

7. The method according to claim 1, wherein the peptide is administered subcutaneously.

8. The method according to claim 1, wherein the peptide is administered intramuscularly.

9. The method according to claim 1, wherein the peptide is administered intracerebroventricularly.

10. The method according to claim 1, wherein the peptide is administered intrathecally.

11. The method according to claim 1, wherein the peptide is administered transdermally.

12. The method according to claim 11, wherein the transdermal administration is by iontophoresis.

13. The method according to claim 1, wherein the mammal is undergoing reperfusion.

14. The method according to claim 13, wherein the reperfusion is a treatment for ischemia.

15. The method according to claim 14, wherein the ischemia is due to stroke.

16. The method according to claim 1, wherein the mammal is suffering from sepsis.

17. The method according to claim 1, wherein the mammal is suffering from an inflammatory process.

18. The method according to claim 17, wherein the mammal is suffering from arthritis.

19. The method according to claim 1, wherein the mammal is suffering from diabetes.

20. The method according to claim 1, wherein the mammal is suffering from liver damage.

21. The method according to claim 20, wherein the liver damage is caused by a viral infection.

22. The method according to claim 20, wherein the liver damage is caused by a toxic agent.

23. The method according to claim 1, wherein the mammal is a human.

24. A method of reducing oxidative damage in a removed organ of a mammal, the method comprising administering to the removed organ an effective amount of D-Arg-Dmt-Lys-Phe-NH$_2$ peptide.

* * * * *

UNITED STATES PATENT AND TRADEMARK OFFICE
CERTIFICATE OF CORRECTION

| | | |
|---|---|---|
| PATENT NO. | : 7,550,439 B2 | Page 1 of 1 |
| APPLICATION NO. | : 11/040242 | |
| DATED | : June 23, 2009 | |
| INVENTOR(S) | : Hazel H. Szeto | |

It is certified that error appears in the above-identified patent and that said Letters Patent is hereby corrected as shown below:

Claim 6, Column 49, Line 45:

Delete "claim 3" and replace it with --claim 5--.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,550,439 B2 | Page 1 of 1 |
| APPLICATION NO. | : 11/040242 | |
| DATED | : June 23, 2009 | |
| INVENTOR(S) | : Szeto | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 199 days.

Delete the phrase "by 199 days" and insert -- by 651 days --

Signed and Sealed this

Twenty-second Day of June, 2010

David J. Kappos
*Director of the United States Patent and Trademark Office*

SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Tyr Arg Phe Lys Glu His Trp Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Lys Gln Tyr Arg Phe Trp
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: AMIDATION

<400> SEQUENCE: 3

Tyr Arg Phe Lys Glu
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid

<400> SEQUENCE: 4

Met Tyr Lys Phe Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-amino acid

```
<220> FEATURE:
<221> NAME/KEY: MISC_FEATURE
<222> LOCATION: (5)..(5)
<223> OTHER INFORMATION: D-amino acid

<400> SEQUENCE: 5

His Glu Lys Tyr Phe Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MOD_RES
<222> LOCATION: (6)..(6)
<223> OTHER INFORMATION: AMIDATION

<400> SEQUENCE: 6

Lys Gln Tyr Arg Phe Trp
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid

<400> SEQUENCE: 7

Phe Arg Lys Trp Tyr Arg His
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MOD_RES
<222> LOCATION: (7)..(7)
<223> OTHER INFORMATION: AMIDATION
```

-continued

```
<400> SEQUENCE: 8

Gly Phe Lys Tyr His Arg Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MOD_RES
<222> LOCATION: (8)..(8)
<223> OTHER INFORMATION: AMIDATION

<400> SEQUENCE: 9

Val Lys His Tyr Phe Ser Tyr Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid

<400> SEQUENCE: 10

Trp Lys Phe Asp Arg Tyr His Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MOD_RES
<222> LOCATION: (8)..(8)
<223> OTHER INFORMATION: AMIDATION

<400> SEQUENCE: 11

Lys Trp Tyr Arg Asn Phe Tyr His
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid

<400> SEQUENCE: 12

Thr Gly Tyr Arg His Phe Trp His Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: AMIDATION

<400> SEQUENCE: 13

Asp Trp Lys Tyr His Phe Arg Gly Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
```

-continued

```
<220> FEATURE:
<221> NAME/KEY: MOD_RES
<222> LOCATION: (10)..(10)
<223> OTHER INFORMATION: AMIDATION

<400> SEQUENCE: 14

His Lys Tyr Phe Glu Asp His Lys Arg Trp
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid

<400> SEQUENCE: 15

Ala Phe Arg Tyr Lys Trp His Tyr Gly Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid

<400> SEQUENCE: 16

Tyr His Phe Arg Asp Lys Arg His Trp His Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
```

```
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid
<220> FEATURE:
<221> NAME/KEY: MOD_RES
<222> LOCATION: (11)..(11)
<223> OTHER INFORMATION: AMIDATION

<400> SEQUENCE: 17

Phe Phe Tyr Arg Glu Asp Lys Arg Arg His Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (11)..(11)
<223> OTHER INFORMATION: D-amino acid

<400> SEQUENCE: 18

Phe Tyr Lys Arg Trp His Lys Lys Glu Arg Tyr Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid

<400> SEQUENCE: 19

Tyr Asp Lys Tyr Phe Lys Arg Phe Pro Tyr His Lys
1               5                   10
```

```
<210> SEQ ID NO 20
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (13)..(13)
<223> OTHER INFORMATION: D-amino acid
<220> FEATURE:
<221> NAME/KEY: MOD_RES
<222> LOCATION: (13)..(13)
<223> OTHER INFORMATION: AMIDATION

<400> SEQUENCE: 20

Glu Arg Lys Tyr Val Phe His Trp Arg Gly Tyr Arg Met
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(3)
<223> OTHER INFORMATION: D-amino acids
<220> FEATURE:
<221> NAME/KEY: MISC_FEATURE
<222> LOCATION: (7)..(7)
<223> OTHER INFORMATION: D-amino acids
<220> FEATURE:
<221> NAME/KEY: MISC_FEATURE
<222> LOCATION: (9)..(9)
<223> OTHER INFORMATION: D-amino acids
<220> FEATURE:
<221> NAME/KEY: MISC_FEATURE
<222> LOCATION: (11)..(11)
<223> OTHER INFORMATION: D-amino acids
<220> FEATURE:
<221> NAME/KEY: MISC_FEATURE
<222> LOCATION: (13)..(13)
<223> OTHER INFORMATION: D-amino acids

<400> SEQUENCE: 21

Arg Leu Tyr Phe Lys Glu Lys Arg Trp Lys Phe Tyr Arg Gly
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(5)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (12)..(12)
<223> OTHER INFORMATION: D-amino acid
<220> FEATURE:
<221> NAME/KEY: MOD_RES
<222> LOCATION: (15)..(15)
<223> OTHER INFORMATION: AMIDATION

<400> SEQUENCE: 22

Glu Asp Lys Arg His Phe Phe Val Tyr Arg Tyr Tyr Arg His Phe
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (6)..(7)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (12)..(12)
<223> OTHER INFORMATION: D-amino acid
<220> FEATURE:
<221> NAME/KEY: MISC_FEATURE
<222> LOCATION: (14)..(14)
<223> OTHER INFORMATION: D-amino acid

<400> SEQUENCE: 23

Asp Arg Phe Cys Phe Arg Lys Tyr Arg Tyr Trp His Tyr Phe Lys Phe
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (11)..(11)
<223> OTHER INFORMATION: D-amino acid
```

```
<220> FEATURE:
<221> NAME/KEY: MISC_FEATURE
<222> LOCATION: (14)..(14)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 24

His Tyr Arg Trp Lys Phe Asp Ala Arg Cys Tyr His Phe Lys Tyr His
1               5                   10                  15

Ser

<210> SEQ ID NO 25
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (10)..(11)
<223> OTHER INFORMATION: D-amino acid
<220> FEATURE:
<221> NAME/KEY: MISC_FEATURE
<222> LOCATION: (15)..(15)
<223> OTHER INFORMATION: D-amino acid
<220> FEATURE:
<221> NAME/KEY: MISC_FEATURE
<222> LOCATION: (18)..(18)
<223> OTHER INFORMATION: D-amino acid

<400> SEQUENCE: 25

Gly Ala Lys Phe Lys Glu Arg Tyr His Arg Arg Asp Tyr Trp His Trp
1               5                   10                  15

His Lys Asp

<210> SEQ ID NO 26
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: D-amino acid
<220> FEATURE:
<221> NAME/KEY: MISC_FEATURE
<222> LOCATION: (9)..(10)
<223> OTHER INFORMATION: D-amino acid
<220> FEATURE:
<221> NAME/KEY: MISC_FEATURE
<222> LOCATION: (13)..(13)
<223> OTHER INFORMATION: D-amino acid
<220> FEATURE:
<221> NAME/KEY: MISC_FEATURE
<222> LOCATION: (17)..(17)
<223> OTHER INFORMATION: D-amino acid
<220> FEATURE:
<221> NAME/KEY: MOD_RES
<222> LOCATION: (20)..(20)
<223> OTHER INFORMATION: AMIDATION
```

```
<400> SEQUENCE: 26

Thr Tyr Arg Lys Trp Tyr Glu Asp Lys Arg His Phe Tyr Gly Val Ile
1               5                   10                  15

His Arg Tyr Lys
            20

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: 2',6' dimethylt
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: AMIDATION

<400> SEQUENCE: 27

Tyr Arg Phe Lys Cys
1               5
```